(12) United States Patent
Solomon et al.

(10) Patent No.: US 8,231,902 B2
(45) Date of Patent: *Jul. 31, 2012

(54) SEGMENTED PHARMACEUTICAL DOSAGE FORMS

(75) Inventors: Lawrence Solomon, Boca Raton, FL (US); Allan S. Kaplan, Boca Raton, FL (US)

(73) Assignee: Accu-Break Technologies, Inc., Plantation, FL (US)

( * ) Notice: Subject to any disclaimer, the term of this patent is extended or adjusted under 35 U.S.C. 154(b) by 135 days.

This patent is subject to a terminal disclaimer.

(21) Appl. No.: 10/598,355

(22) PCT Filed: Nov. 18, 2005

(86) PCT No.: PCT/US2005/042120
§ 371 (c)(1),
(2), (4) Date: May 12, 2008

(87) PCT Pub. No.: WO2007/058660
PCT Pub. Date: May 24, 2007

(65) Prior Publication Data
US 2008/0233190 A1 Sep. 25, 2008

(51) Int. Cl.
*A61K 9/44* (2006.01)
(52) U.S. Cl. ............. 424/467; 424/465; 424/472
(58) Field of Classification Search ............ 424/467
See application file for complete search history.

(56) References Cited

U.S. PATENT DOCUMENTS

| | | | |
|---|---|---|---|
| 3,128,226 A | | 4/1964 | Rubin et al. |
| 3,517,871 A | * | 6/1970 | Gaffney et al. ........ 225/103 |
| 3,927,194 A | * | 12/1975 | Geller ................ 424/467 |
| 4,139,589 A | * | 2/1979 | Beringer et al. ........ 264/250 |
| 4,215,104 A | * | 7/1980 | Ullman et al. ......... 424/467 |
| 4,574,080 A | | 3/1986 | Roswall et al. |
| 4,789,546 A | * | 12/1988 | Medri ................ 424/441 |
| 5,158,728 A | | 10/1992 | Sanderson |
| 5,686,109 A | * | 11/1997 | Fujitsu et al. ......... 424/464 |
| 5,817,340 A | | 10/1998 | Roche et al. |
| 6,086,919 A | | 7/2000 | Bauer et al. |
| 6,183,778 B1 | | 2/2001 | Conte et al. |
| 6,294,200 B1 | | 9/2001 | Conte et al. |
| 6,309,668 B1 | | 10/2001 | Bastin et al. |
| 6,827,947 B2 | * | 12/2004 | Lofroth et al. ......... 424/497 |
| 6,919,373 B1 | | 7/2005 | Lam et al. |
| 7,011,849 B2 | | 3/2006 | Storm et al. |
| 2002/0132850 A1 | | 9/2002 | Bartholomaus |
| 2005/0026992 A1 | * | 2/2005 | Sasmal et al. ......... 514/423 |
| 2005/0038039 A1 | | 2/2005 | Fanara et al. |
| 2006/0280794 A1 | | 12/2006 | Hamaguchi et al. |

FOREIGN PATENT DOCUMENTS
CH 648754 4/1985

OTHER PUBLICATIONS

Lieberman, Herbert et al, Pharmaceutical Dosage Forms—tablets, 1990, Informa Health Care, vol. 1, pp. 132 and 274.*
Uroxatral(https://members.kaiserpermanente.org/kpweb/drugency/drugdetails.do?drugID=452334&name=Uroxatral+10+mg+24+hr+Tab&index=true).*
Hess et al (CH 648754; translation provided by USPTO) (1978).*
H.A. Lieberman and L. Lachman, Pharmaceutical Dosage Forms, vol. 1, pp. 217-223, Marcel Dekker, Inc., New York, New York.

* cited by examiner

*Primary Examiner* — Jake M. Vu
(74) *Attorney, Agent, or Firm* — Ted W. Whitlock

(57) ABSTRACT

A pharmaceutical tablet adapted for accurate division of a dose of a drug into two or more smaller doses, which tablet has two or more segments.

5 Claims, 22 Drawing Sheets

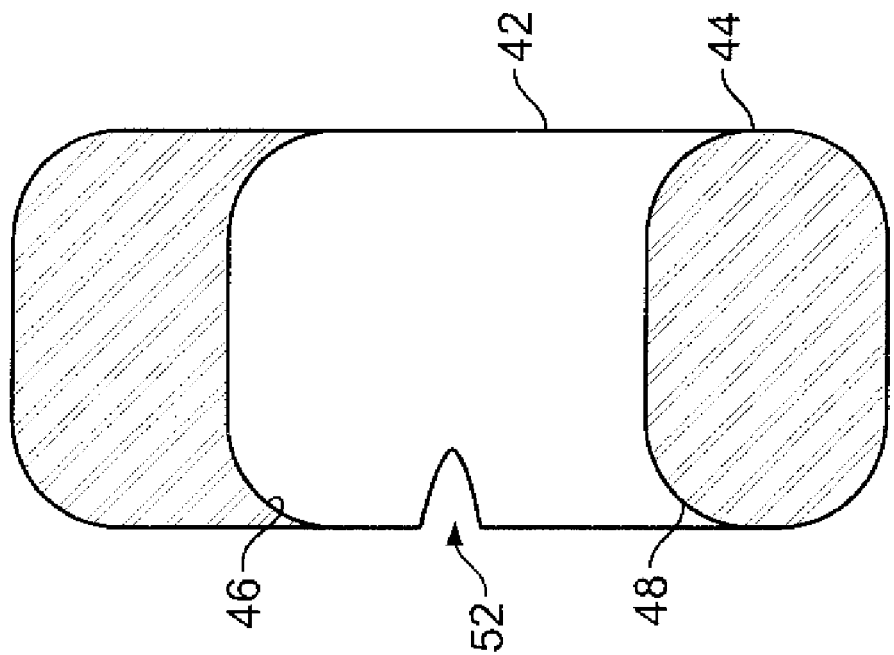
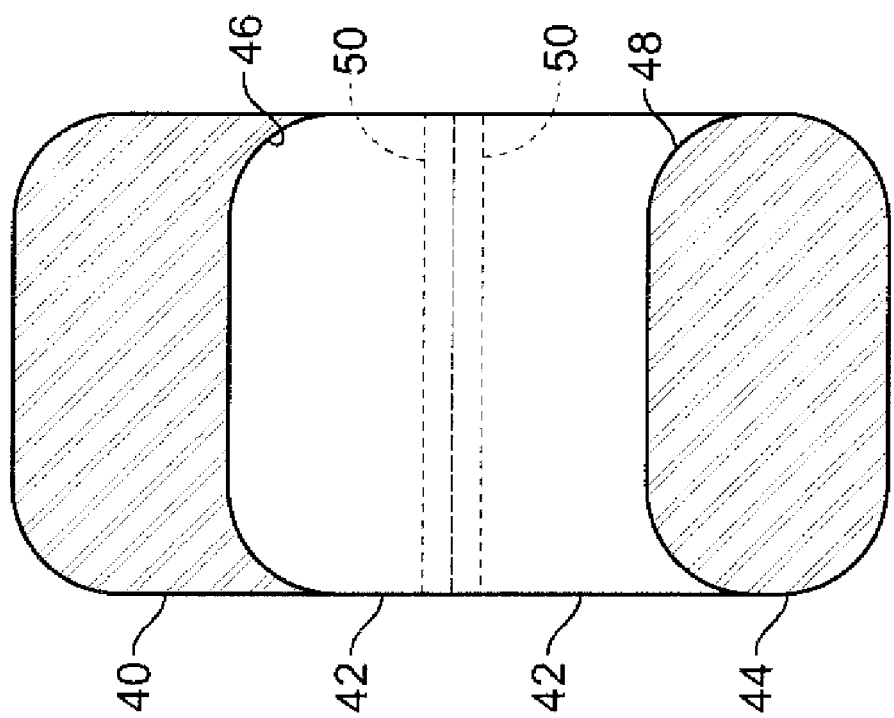

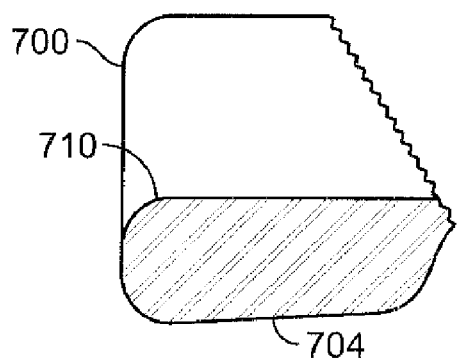 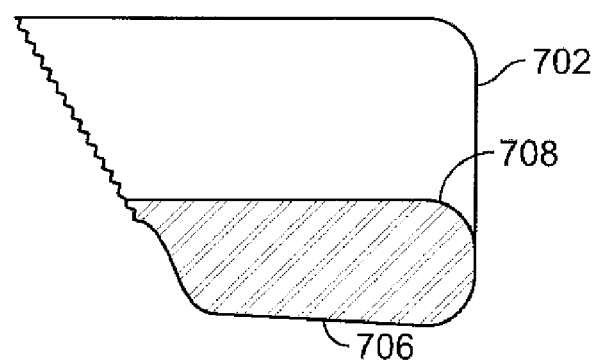
FIG. 14A  FIG. 14B

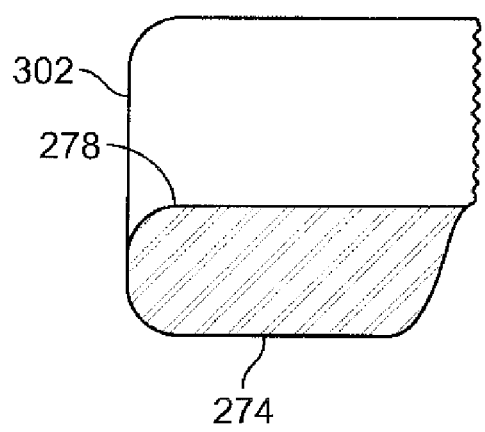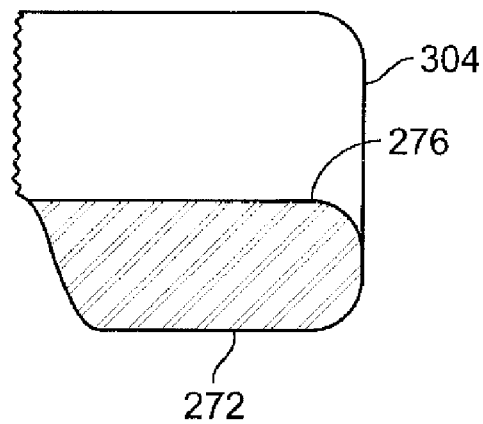
FIG. 17A  FIG. 17B

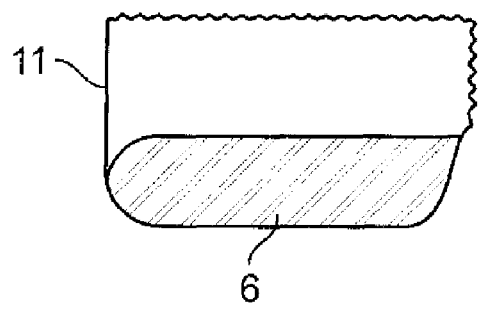 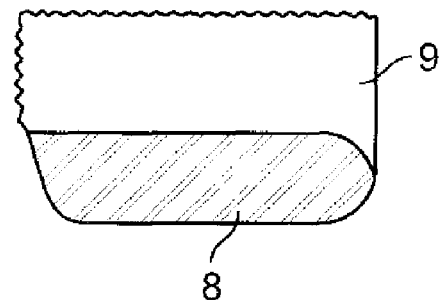
FIG. 22A  FIG. 22B

SEGMENTED PHARMACEUTICAL DOSAGE FORMS

This is a United States national filing under 35 USC 371, claiming the priority benefit of International Application PCT/US05/42120, filed Nov. 18, 2005.

FIELD OF THE INVENTION

The invention involves layered pharmaceutical tablets comprising a layer or segment, containing a drug and a second layer or segment either lacking a drug or containing a drug as part of a different granulation, such as in a less concentrated form, and methods relating thereto. More specifically, the subject invention concerns novel dosage forms and methods for providing divisible, controlled release pharmaceutical products which in preferable embodiments can provide accurate and consistent divided doses. The dosage form can comprise a segment which has a score, which can be a deep score.

BACKGROUND

The invention derives from the need to solve at least two related problems within the pharmaceutical industry: (1) inaccurate or inconsistent dose division upon breaking of a dosage form, and (2) inflexibility in adjusting the dose of only one active ingredient in a combination dosage form.

With regard to the first problem of inconsistent or inaccurate dose division, it is known that pharmaceutical tablets are commonly broken to modify the dose provided by a whole tablet. These dosage adjustments through tablet breaking by patients have been determined to be imprecise. Scoring of pharmaceutical tablets is well known. Scoring of pharmaceutical tablets produced in a layered fashion is also known but has been employed less extensively. Scores into a tablet have not exceeded 1 mm in depth. Tablets are often produced with a score to aid breaking, but such tablet breaking is well-documented to suffer many problems whether or not scoring of the tablet is provided. Even though inaccurate breaking of scored tablets is a well-known problem, attention has not been paid to solving this problem by creating segmented (e.g., layered) tablets in a tablet press with a segment that provides some or most of said breaking region when the tablet is broken, and pari passu provides physical, support for the part of the tablet with the deep score. Many drugs, such as warfarin, require dosage adjustments during treatment and the scored tablets of the marketed warfarin products are frequently broken to achieve this dosage adjustment. These dosage adjustments through tablet breaking by patients have been determined to be imprecise.

Experts for many years have called upon the pharmaceutical industry to improve the quality of tablet breaking, yet such has not been optimized until the current invention. In 1984, Stimpel et al. ("Stimpel"), described the relative accuracy of breaking various tablets for treatment of cardiovascular problems. M. Stimpel et al., "Breaking Tablets in Half," The Lancet (1964):1299. Even though breaking was performed by a sophisticated, dexterous person, Stimpel found that breaking was not accurate, and opined that real world use by patients would provide even more unsatisfactory results.

Rodenhuis et al., (2004) observed that European regulatory authorities, in 1998, started a policy to discourage scoring of tablets. This policy change, according to Rodenhuis, likely related to "many recent reports of bad functioning score lines," that "many scored tablets are difficult to break," and that "many scored tablets show unsatisfactory mass uniformity of the subdivided halves." Rodenhuis reported that 31% of all tablets in one Netherlands study were subdivided before being swallowed. Rodenhuis noted that "[i]mproving the functioning of score lines may be a more practical approach than banning this [scored] dosage form". N. Rodenhuis et al., "The rationale of scored tablets as dosage form." European J. of Pharmaceutical Sciences 21 (2004):305-308. See also, van Santen, E., Barends, D. M. and Frijlink, H. W. "Breaking of scored tablets: a review." European J. of Pharmaceutics and Biopharmaceutics 53 (2002):139-145 for a comprehensive review article on this topic.

Peek et al., (2002), studied tablet splitting by "elderly patients" aged 50-79. Peek, B. T., Al-Achi, A., Coombs, S. J. "Accuracy of Tablet Splitting by Elderly Patients." The Journal of the American Medical Association 288 No. 4 (2002): 139-145. Breaking scored tablets with mechanical tablet splitters without specific instruction led to highly unsatisfactory separating of the tablets. For example, warfarin 5 mg was on average split into 1.9 and 3.1 mg tablets. This potent anticoagulant has such a narrow therapeutic range that 2, 2.5, and 3 mg tablet doses are manufactured. Biron et al., (1999), demonstrated that warfarin 10 mg also often split, to less than 4.25 or greater than 5.75 mg. Biron, C., Liczner, P., Hansel, S., Schved, J. F., "Oral Anticoagulant Drugs Do Not Cut Tablets in Quarters." Throittb Haemost 1201 (1999). In addition, they demonstrated that loss of mass due to crumbling or chipping of the breaking of the warfarin tablets was statistically significant. They also demonstrated that quartering of the tablets was grossly inaccurate.

McDevitt et al., (1998), found that 25 mg unscored hydrochlorothiazide (HCTZ) tablets were manually split badly enough that 12.4% deviated by more than 20% from ideal weight. McDevitt, J. T., Gurst, A. H., Chen, Y. "Accuracy of Tablet Splitting." Pharmacotherapy 18 No. 1 (1998):193-197. 77% of the test subjects stated they would be willing to pay a premium for individually produced HCTZ 12.5 mg tablets rather than split unscored 25 mg tablets.

Rosenberg et al., studied pharmacist-dispensed split tablets. Rosenberg, J. M., Nathan, J. P., Plakogiannis, F. "Weight Variability of Pharmacist-Dispensed Split Tablets," Journal of American Pharmaceutical Association 42 No. 2 (2002): 200-205. They found that "tablet splitting resulted in an unacceptably high incidence of weight variation" and recommended that "standards should be developed to ensure uniformity of split tablets."

Teng et al., (2002), using a trained individual in a laboratory setting to split tablets, concluded that "the majority of the 11 drug products we tested, when assessed for their: ability to be split into half-tablets of equal dose, failed a liberally interpreted USP (United States Pharmacopoeia) uniformity test . . . . The practice of dividing tablets to save costs or to improve a dosage regimen . . . is not recommended for patients using drugs with more substantial toxicity and steep dose-response efficacy curves." Teng, J., Song, C. K., Williams, R. L., Polli, J. E. "Lack of Medication Dose Uniformity in Commonly Split Tablets." Journal of American Pharmaceutical Association 42 No. 2 (2002):195-199.

In the U.S., many "managed care" insurance organizations recommend or encourage patients to split or divide tablets, including unscored or irregularly-shaped tablets. Many drug products in the US are unscored or are provided as capsules despite being able to be formed as tablets. The dosage forms and methods of the subject invention can advantageously provide a patient with the capability to comply with such recommendations by the managed care insurance organizations A second problem arising from dividing or breaking a dosage form relates to combination drug products, i.e., single or unitary dosage forms containing two or more active ingredients. Combination dosage forms are typically produced as homogeneous mixtures or as capsules. A physician prescribing these combination products, such as a combination product currently available to treat arterial hypertension, may not adjust the dose of only one active ingredient in the combination product without a consequent proportional adjustment to the dose of the other active ingredient(s).

Combination dosage forms can thus be disadvantageous due to the inflexibility of dealing with changing circumstances such as fluctuating blood pressure or the appearance of side effects to a drug. An adjustment to the dose of one of the active ingredients in a commonly available combination product necessarily results in the dose adjustment of the other active ingredient or ingredients contained in that same dosage form. Clearly, dividing a tablet or capsule containing a homogeneous mixture of two or more active ingredients divides each of the active ingredients in that homogeneous mixture. Even if the actives are layered separately, the layer configuration of currently available combination dosage forms is such that breaking of the tablet results in breaking through all layers, thus dividing all active ingredients proportionally. This disadvantage has been propounded many times over the years, and has hindered the acceptability of certain combination products, for example, in treatments for arterial hypertension ("hypertension"). Nevertheless, even with these disadvantages, combination treatments for hypertension have proven popular for cost and potential compliance reasons. Accordingly, there is a need for combination products which can provide the flexibility of adjusting the dose of one of the actives without necessarily adjusting the dose of the other active(s) contained within the combination dosage form.

There is no controlled release dosage form provided in the prior art that fully addresses these problems facing the industry. The prior art does not describe a dosage form having two layers of active drug or drugs, at least one of which is a controlled release layer, in different places within a tablet with an interposed different layer that can be broken through by application of manual pressure to accurately and consistently provide modified or divided doses of the active drug or drugs.

Certain combination drug products have been described or marketed having the two or more active ingredients provided in different layers. For example, U.S. Pat. No. 5,738,874 to Conte, et al. describes a multi-layer controlled release tablet having a first layer comprising an immediate release drug composition, a second layer comprising a slow release drug composition, and a third layer comprising a barrier composition to modify release of drug from the layer adjacent thereto. This third, drug-free layer is not interposed between the drug-containing layers and is not useful for facilitating breakage or splitting of the tablet.

Published U.S. Application 2005/0019407A1 describes a composite dosage form which has first and second portions joined at an interface. These dosage forms have a first molded material and a second compressed material. There is no disclosure of any modification of the disclosed dosage forms that would facilitate the breaking of the dosage forms into any subdivided form.

U.S. Pat. No. 6,602,521 describes a multiplex drug delivery system containing at least two immediate release drug dosage packages enveloped by a scored, extended release compartment. There is no teaching from the disclosure of this patent of a controlled release compartment which does not envelop the immediate release compartments.

Combination products having at least two layers comprising active drug, separated by an interposed inactive layer (i.e., one derived from a granulation lacking drug) are known. However, these prior art dosage forms are provided only when there is a physical or chemical incompatibility between the different layers containing active drug. In that case of incompatible active layers, the prior art specifically teaches that said "separating layer" be of as limited a size as is necessary to separate the incompatible layers.

Commercially, the only pharmaceutical product to our knowledge that is produced as a taller-than-wide dosage form is Concerta®, which is a layered tablet, having a semi-permeable membrane and utilizes the ORGS® system for its controlled release characteristics. The manufacturer's directions for the use of Concerta® specify that the tablets should never be broken. Concerta® does not include a score and does not include an inactive layer interposed between, and therefore separating, active controlled release layers. Except for Concerta®, tablets have not been produced that are wider than they are tall, including those involving layers vertically disposed one on the other.

The present invention, as disclosed herein, can overcome or alleviate both of the problems discussed above, and can provide additional advantages and address additional problems as would be well understood and recognised in the art.

SUMMARY OF THE INVENTION

The subject invention relates, generally, a tablet advantageously adapted for separating one vertically disposed segment from another. The present invention concerns configuring pharmaceutically active formulations, e.g., granulations comprising at least one active drug, in different parts of a compressed tablet and, preferably, with an inactive layer interposed between the active formulations. In the case of incompatible active drug formulations, the interposed separating layer is of a height different from, preferably greater than, the current teaching regarding layered dosage forms comprising incompatible formulations. In a preferred embodiment, the separating layer is of dimension (e.g., height, as defined or referred to herein) adequate to allow breakage transversely through the separating layer without consequent breakage of other tablet segments.

The subject invention provides a pharmaceutical tablet with at least two different vertically disposed layers which, when compressed, form tablet segments, said tablet comprising a drug or drugs, in which at least one segment comprising drug is provided as a controlled release formulation, and:

(a) said tablet includes two or more segments and each segment either contains the same concentration or amount of a drug, or the same concentrations or amounts of two or more drugs at substantially the same ratio; or else said segment lacks any pharmacologically effective dose of a drug or combination of drugs; or (b) said tablet includes a first segment containing a drug or drugs; a third segment containing a drug or drugs which are different from the drug or drugs in said first segment and said first and third segments are physically and chemically compatible; and a second segment that is interposed between said first and third segments and that has an undetectable amount of, or else a pharmacologically ineffective amount of, any drug present in said tablet; or (c) said tablet includes a first segment containing a drug or drugs, a third segment containing a drug or drugs which are different from the drug or drugs in said first segment and wherein components of said first and third segments are physically or chemically incompatible, and a second segment that is interposed between said first and said third segment and that has an undetectable amount of, or a pharmacologically ineffective amount of, any drug present in said tablet; said third segment has a height of at least 1.5 mm.

In accordance with the subject invention, at least one of the segments comprising active ingredient is formulated as a controlled release composition. The dosage forms of the subject invention are therefore considered as controlled release dosage forms. Thus, for example, controlled release tablets of a three-segment embodiment of the subject, invention comprise longitudinally compressed tablets having two "outer" layers or segments and an "inner" layer disposed therebetween. The outer segments preferably comprise a first layer containing active drug ingredient, generally termed the "upper" or "top" segment, and a second layer containing active drug ingredient, generally termed the "lower" or "bottom" segment. The inner segment, preferably comprises a third, separating layer, preferably substantially free of active drug ingredient, disposed between the top and bottom layers. The interposed inner layer preferably contacts another layer at only one interface, and does not encompass or envelope any other layer or segment of the tablet.

Alternative embodiments of the preferred core tablets of the invention can be, but are not limited to, vertically compressed tablets having at least two compositionally distinct segments, with a first segment containing an active drug and a second segment that:
(a) contains the same drug at a lower concentration than the concentration of said drug in said first, segment, concentration being dependent on weight/weight, ratios of active drug or drugs to excipients within a segment; or
(b) has no detectable drug or the same drug which is in said first segment in a pharmacologically ineffective amount, and said tablet also includes a third segment having the same drug that is present in said first, segment; or
c) has a combination of said drug that is present in said first segment with another drug or drugs not present in a pharmacologically effective quantity or not detectable in said first segment; or
(d) has no detectable drug or the same drug as in said first segment but in a pharmacologically ineffective amount, and said tablet also includes a third segment having a different drug from the drug present in the first segment where the components of said third segment are compatible with the components of said first segment;
(e) has no detectable drug or the same drug which is in said first segment in a pharmacologically ineffective amount, and said tablet also includes a third segment having a different drug from the drug that is present in said first segment, said second segment having a vertical height of at least 3 mm; or
(f) has a different drug than the drug in said first segment and said tablet also includes a third segment having the same drug that is present in said first segment.

Additional segments containing pharmaceutically inactive ingredients, active compositions identical to another segment, or active compositions different from another segment, as well as combinations of active compositions, can also be included as part of the tablet to provide four or more, preferably about four to nine, layered, segments within the tablet. In these further embodiments, certain inner segments can comprise active compositions, which are interposed between an outer and inner segment, or between two inner segments. The number of layers or segments is limited only by the layer press equipment available, and the practicality of the finished product.

In the embodiments of the invention listed above, at least one of the layers or segments within the pharmaceutical tablets is an "altered release", or "controlled release" composition. The terms "altered release" and "controlled release" are contemplated to include a dosage form or composition that has the property of releasing active ingredient from the dosage form at a modified, or "altered" rate relative to the rate of release of drug from a conventional "immediate release" formulation, as would be well understood in the art. Therefore, the term "altered release" includes "controlled release", "delayed release", "extended release", "long-acting", "modified release", "slow release", "sustained release", "time release", and the like, all of which are understood to refer to a release which is later or slower than "immediate release." However, "altered release" may also mean a release rate which is more rapid than a conventional immediate release tablet, for example, a rapid-dissolve tablet or quick-dissolve tablet, which dissolves in the mouth or buccal area before being swallowed, as is also well known and understood in the pharmaceutical industry. A release which is delayed due formulation with enteric or other materials, though releasing immediately following the delay, is understood in the art to be a type of "controlled release", and is so considered for purposes of the subject invention, "Slow release", "extended release", "long-acting", "sustained release", "time release", and the like, are generally recognized as being synonymous and may be used interchangeably herein to designate an "altered release" or "controlled release" formulation which is not "delayed release". The term "intrinsically altered release" refers to a controlled release property of a pharmaceutical composition, e.g., a granulation, whereby the release rate of drug or drugs from that composition is affected by the ingredients or excipients of that composition and not a device or composition that is extrinsic to that composition, e.g., a coating or membrane disposed onto or formed around the composition.

The terms "active agent," "active drug," "drug," "active pharmaceutical ingredient" and "pharmacologically active agent" may be used interchangeably herein to refer to a chemical material or compound which, when administered to an organism (human or animal) induces a pharmacologic effect, and which includes prescription and non-prescription pharmaceutical compounds, and such substances as pharmacologically effective doses of vitamins or co-factors, minerals, including biologically effective salts, and the like.

Tablets of the invention belong to the class of controlled release pharmaceutical tablets formulated with two or more layers, at least one of which is a controlled release composition, and are thus non-homogeneous. One preferred embodiment of the invention is a pharmaceutical tablet having two or more segments, has a top and a bottom, and has a height that, exceeds the width of said tablet, i.e., the tablet is taller than it is wide, said height being measured vertically from the top to the bottom of said tablet while it is in the tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides. The terms "vertical" and "horizontal" ("horizontal" is also referred to as "transverse") axis of the tablets of the invention are determined by and have the same orientation as that of the tablet die in which the tablet is compressed in a tablet press or other tabletting machine ("tablet press" herein), and the order of entry of granulations into the die.

Taller than wide tablets of the invention are shaped to be more easily broken through a tablet's theoretical vertical axis (i.e., in a horizontal direction) than are conventional, currently-manufactured tablets, having a "wider than tall" configuration. Many preferred uses of tablets of the invention are to break through an interposed, segment of the tablet lacking a pharmacologically effective dose of a drug without breaking through a segment above or below said interposed segment.

In another preferred embodiment, the subject, invention concerns a controlled release compressed pharmaceutical tablet that has two or more segments, wherein a first, segment includes a pharmacologically effective amount of a drug or drugs and has a deep score that, extends up to about 50% or greater into said first segment. More preferably, in one embodiment, the score can be formed from 70% to 99.5% of the distance from a surface of said first segment towards an opposite face (surface) of said first segment having on said, opposite face, an adjoining second segment. In an alternative embodiment, the score is formed completely through the first segment and can extend into the second, adjoining segment. In a preferred embodiment, said second segment has an undetectable amount of drug up to a maximum of 80% of the concentration, of the drug in said first segment.

Tablets of the invention are adapted to be useful not only as whole tablets but also to be breakable into subunits known herein as "tablettes", with accurate dosing both as whole tablets and in tablette form. The invention achieves these ends by utilizing in most of its preferred embodiments a segment that comprises a granulation, that can be substantially free of active drug (an "inactive granulation" or "inactive segment").

It is one primary object of the invention to create controlled release pharmaceutical tablets adapted to be broken when it is desired to create a lower dosage (including a dosage of zero) of a drug or drugs present in the whole tablet, by allowing breaking through a segment, preferably, for example, through an inactive segment. An "inactive segment" is substantially free of active drug, and therefore can include a minimal concentration of drug or mixture of drugs (on a w/w basis) or a pharmacologically ineffective quantity of drug or mixture of drugs. Alternatively, the segment being broken through can be a segment that contains a more than minimal, but a decreased, concentration of a drug relative to another segment in the tablet (a "relatively inactive segment").

It is another primary object of the invention to apply the invention both to accurate dosing of single agent products and to combination products.

With regard to the use of the subject invention for combination products, it is understood that a mixture of drugs within one granulation acts as a single drug in a granulation from the standpoint of the separability of one segment from another. In a preferred embodiment in which, for example, Drug A is present in a therapeutically effective quantity in an upper segment, an inner segment that lacks a pharmacologically effective quantity of any drug is interposed between two outer (i.e., top and bottom or upper and lower) segments, and Drug B is present in a therapeutically effective quantity in a lower segment, then the invention can be useful in the situation that the height and especially the "effective height" of said inner segment is great enough to allow said inner segment to serve as the breaking region of said tablet substantially without breaking through either outer segment. The prior art, however, is such that novelty for the subject invention requires no minimum height of said inner segment if, in said tablet, all ingredients of the upper and lower segments are physically and chemically compatible with each other.

In the specialized situation in which there is an incompatibility between components of said outer segments, then the prior art is such that any inner "separating" segment should be limited in height to the minimum needed to eliminate the presence of any of said incompatibilities, for such reasons as to minimize the size of the tablet as a whole or to minimize cost. In that case, the invention remains novel in any of its more preferred forms, in which there is provided, relative to a quantity provided solely to separate incompatible layers, as is known, an excess quantity of said inner separating segment to allow it to be broken.

BRIEF DESCRIPTION OF THE DRAWINGS

FIG. 1a is a cross-section of a taller than wide tablet looking towards the side of the tablet that has a score;

FIG. 1b is a cross-section of the tablet of FIG. 1a looking at the side of the tablet where the score ends;

FIGS. 14a and 14b are views of FIG. 12 when the tablet has been broken at an angle from vertical.

FIGS. 17a and 17b depict two tablettes formed by splitting the tablet of FIG. 16 through the top of the score.

FIG. 19b is an en face external view of the same tablet shown in FIG. 19a.

FIGS. 22a and 22b demonstrate the tablettes formed by breaking the tablette of FIG. 22b as guided by the score.

Figure 2C:
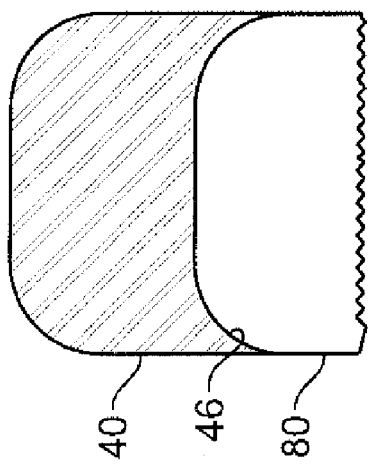
FIGS. 2a-b and 2c-d are views of FIG. 1a and FIG. 1b respectively when the tablets have been broken through the score.

All of the whole tablets referenced above comprise at least one segment that intrinsically has an altered-release characteristic.

The tablets of the invention comprise at least two compositionally different segments.

DETAILED DESCRIPTION OF THE INVENTION

All of the whole tablets described and shown herein comprise at least one segment that intrinsically has an altered-release characteristic. Intrinsic altered release characteristic refers to the release property of the composition itself, i.e., altered or controlled release (as compared to immediate release) of drug or drugs from the composition without the use of a device or composition, such as a coating or membrane or the like, that is extrinsic to the segment composition for altering or controlling said release.

The tablets of the invention will comprise at least two compositionally different segments.

Tablets of the invention are described herein. All segments that substantially lack drug activity are intrinsically of immediate release nature. The tablets are therefore of altered release or controlled release nature due to the composition of the one or more segments that is intentionally formulated to have such an altered release property.

Tablets of the invention are preferably produced on a layer press, such as a tri-layer or five-layer high speed press manufactured by Korsch AG of Germany. Remington's Pharmaceutical Sciences 20th Ed., Mack-Publishing Co., Easton, Pa. (2000), Chapter 45, which is incorporated by reference, describes the various techniques utilized in making compressed tablets. The tablets of the invention are primarily intended for oral administration but they may also be used for other applications. Except for an excipient having adhesive properties used within a layer or segment formulation, tablets of the invention are not formed using a cement, glue, adhesive, or the like, and are preferably uncoated.

The tablets are formed from compressing, e.g., vertically, at least two different pharmaceutical formulation compositions, e.g., granulations, configured as separate layers or tablet segments; more preferred tablets comprise three vertically disposed segments. Embodiments of the subject invention include, but are not limited to, a vertically compressed tablet having a height greater than its width (a "taller than wide" tablet), and a unitary segmented tablet. These embodiments can comprise a separation mark or score.

A layer is produced by introducing an amount of an individual granulation into a tablet die to fill at least a part of the die. A layer is considered to be present whether it is the form of an un-tamped, tamped or fully compressed granulation.

As an example of a method of manufacture of a preferred tablet of the invention, first, a granulation containing a pharmacologically effective dose of a drug enters the die and is tamped to form a first segment. Second, a granulation lacking a drug (an "inactive granulation") enters the die and is tamped. The inactive granulation creates a part of the tablet that can be identified and broken through so that a part of the drug containing a significant concentration of drug is not broken through. Last, a second granulation containing a pharmacologically effective quantity of a drug enters the die, is optionally tamped, and then final compression to form a third segment and a final compressed tablet occurs. While one or all segments may individually have a width greater than height, the tablet as a whole has a height that exceeds its width.

Suitable dimensions for tablets according to the invention are: height: 6 to 24 mm; preferably 10 to 18 mm and more preferably from 10 to 14 mm; width (at the widest dimension of the horizontal axis): 2 to 16 mm; preferably 3 to 10 mm and more preferably 4 to 8 mm. Without, limitation, the dimensions of the tablet may be optimal if the ratio of the height to the width is between about 1.5:1 to about 3:1.

Subsequent to tablet formation, optionally a score may be placed in the side of said tablet, preferably transversely. Alternatively, after tablet, formation, a printed line or other forms of indicia such as dotted lines, symbols or perforations may be placed on or in the surface of the tablet, all of which serve the purpose of allowing identification of said, tablet's desired breaking region from the standpoint of effecting accurate separation of the parts of a tablet containing isolated doses of drug. Other means of aiding identification of a region of potentially desired tablet breaking may be utilized such as the use of contrasting colors in different segments.

Additionally, the compressed tablet can be further processed to provide an inert covering, e.g., a gelatin capsule or a sachet. In use, the covering can be cut away or otherwise removed, such as by twisting apart, a conventional gelatin capsule, removing the tablet therein and dividing the tablet as described herein for a non-encapsulated embodiment. Alternatively, a separation mark provided on the capsule or sachet can guide a user to divide the tablet and its covering at a designated site in order to effect an accurate splitting of a tablet of the subject invention. The covering can advantageously be useful to minimize or prevent, confusion on the part of the patient user viewing a segmented or layered tablet of the subject invention.

In certain of the preferred tablets of the invention, a layer (and the granulation from which it is derived) will not need to be placed on top of or below (e.g., adjoining, or contiguous with) a substantially identical layer (or granulation). In such a case, one layer will give rise to the sub-type of segment that is a simple segment. The use of the term "segment" allows a segment to be simple or compound. Because the tablets of the invention have been adapted to be broken if and when desired, a term for the major fragments resulting from said breaking has been coined. The inventors use the term "tablette" in this regard.

An example of tablette formation is as follows: a standard single-scored, mono-layer, homogeneous pharmaceutical tablet is broken. Said breaking produces two major fragments, each of which is called a tablette. Some chipping and crumbling, which are preferably minor in amount, may occur in the segmented, layered tablets of the invention, to utilize the invention properly may make it advantageous to place a score transversely into a segment, such as an inner segment, as may be done with an instrument such as a file. Successfully breaking said tablet through said score will result in two table ties, representing the two major fragments of the tablet and net including smaller-fragments such as crumbs or chips.

Of the many tablets than can be produced according to the invention, an example of a tablet manufactured in a multilayer tablet press is:

A first granulation comprising drug A enters into a die at a first filling station; a second granulation comprising inactive excipients enters on top of said first granulation at a second filling station; a granulation substantially identical in composition and quantity (weight) to said first granulation enters at a third filling station. After final compression, said tablet is ejected from the die. Each granulation, upon full entry into the die and thereafter, forms a layer, or segment, of the final tablet product.

Ideally, in any of the manufacturing processes employed to form a tablet of the subject invention, there is no mixing of drug or excipients from one segment to another. However, in reality, minimal, inadvertent mixing between different granulations in the formation of layers can occur. Therefore, some mixing is to be expected and does not alter the improvement in the art of creating accurate dosing from breakable tablets from the invention. Different granulations may be of the same or different colors. Wet granulations are often preferred to limit transfer of material from one granulation to another. Direct compression of powder is also a preferred manufacturing technique.

By convention herein, the term "segments" may be used in place of "layers" in general in discussing the finished tablets of the invention, for reasons that, are explained below. In addition, for convenience of reference and consistency throughout this specification, the descriptions herein may refer to the segments as comprising or utilizing a particular "granulation". Such term is not limited to the formation of granules, per se, as in a wet granulation process. Other formulation compositions, for example, homogeneous mixtures or blends used, in direct compression matrix formulations, coated or uncoated beads or pellets used in compressed tablets, or like compositions as are well known in the art and suitable for use in conventional layered, compressed tablet technologies, can be readily substituted for such "granulations" and are considered within the scope of the invention. It is expressly intended that the subject invention include each of these alternatively available and well known compressible formulation technologies.

A segment represents the entirety of a substantially homogeneous contiguous part of a tablet. A segment may be formed from more than one layer, however: If two substantially identical granulations entered the tablet die successively, with the second entering directly after and onto the first, such as at two successive filling stations during automated high-speed tablet manufacture, then the two granulations would each form a separate layer after entering, but when compressed, they would comprise one segment. A segment therefore is a basic unit of how the tablets of the invention prove useful. If, however, two different active drugs, or different salts of the same active drug, were compressed one on top of the other, they would form two segments. Granulations comprising the same active drug but with dissimilar excipients would also form two segments if one granulation were compressed onto another.

A segment formed by a plurality of layers that are formed from substantially identical granulations is called a compound segment. Compound segments may prove useful in situations of relatively large quantities of an inactive granulation, or granulation containing a drug or drugs, so that two or more consecutive fills ("feeds") of substantially identical granulation may occur.

A layer formed from a granulation that is neither disposed upon nor under (i.e., does not adjoin and is not contiguous with) a substantially identical granulation is a simple segment. A non-compound segment is a simple segment.

As used herein, such terms as "horizontal" ("transverse") and "vertical" when used in relation to a tablet, are based on the spatial orientation of the tablet as, and after, it is produced in a die, but before removal or ejection from the die. Current methods of manufacture produce tablets with one granulation entering the die on top of another, so that, tablets of the invention produced in such a manner comprise one or more top (outer) segments, one or more bottom (outer) segments, and optionally one or more middle (inner) segments. A segment that is not a top or bottom (i.e., outer) segment is considered to be an inner segment.

In any configuration of a tablet according to the subject invention, the lateral parts of any outer or inner segment have an externally exposed surface.

If separate granulations were to be sequentially placed in a die horizontally (side-to-side) and not vertically as is currently the practice, then, the tablets so produced would be within the scope of the present invention because the same resultant product would be produced by the horizontal compression process. When the tablet of FIG. 1, for example, is laid on a flat table, it will tend to lie lengthwise at right angles to the manner in which it is formed in the die, so that if the three segments were all different colors, then the segments would appear to be arranged not vertically (one on top of the other), but rather horizontally (side-to-side). For consistency of terminology, such segments nonetheless are considered herein to be disposed vertically on top of each other.

Tablets of the invention are preferably uncoated, but can be coated with conventional coatings for aesthetic or functional or other purpose. However, these coatings are not regarded as a "layer" or "segment" of the tablets of the subject invention. These coatings do not significantly alter the release kinetics of the drug or drugs of the tablets of the invention.

The terms "active agent," "drug," "active drug," "active pharmaceutical agent," and "pharmacologically active agent" are interchangeable and include, without limitation, prescription and non-prescription pharmaceutical compounds, as well as pharmacologically effective doses of vitamins, cofactors, and the like. Substances such as foodstuffs, vitamins in "recommended daily allow" quantities, and the like are not considered to be "drugs" herein.

The term "undetectable amount" means that when using conventional analytical techniques such as high performance liquid chromatography (HPLC), nuclear magnetic resonance imaging (NMRI), and the like, the presence of an active compound can not be identified. The term "pharmacologically ineffective amount" means an amount of a drug or drugs that has or have no measurable pharmacological effect. Due to the conditions under which high speed automated tabletting equipment are operated, mixing of different granulations may occur during tablet formation which may cause material such as drug substance present in one granulation to appear in a layer or segment where it was not intended to be placed.

The term "relatively inactive segment" refers to a segment that either contains an undetectable amount of any drug or contains a decreased concentration of any drug or drugs contained in another segment or segments in a pharmacologically effective quantity. The term "decreased concentration" means that the concentration of a drug or drugs in said relatively inactive segment is no more than 80% that of said drug or drugs in another segment, more preferably no more than 20% of said other segment's drug or drugs concentration; most preferably said ratio is no more than 5%, however. The concentration of a drug or drugs in a segment means, herein, the ratio, on a weight to weight basis, of the drug or drugs in said segment to the total weight of said segment, which includes said drug or drugs and inactive excipients.

The tablets of the invention are preferably broken transversely in order to realize their benefits or advantages. They may be broken in standard ways, according to the invention such as either by applying force manually (or "by hand" as the term is commonly understood) to cause the tablet to break at a desired location, or by use of an instrument, such as a cutting edge, to apply force directly to a separation mark provided in a desired breaking region.

Separation marks are intended to guide optional tablet breaking in the usual manner that is well known with scores, so that, if tablet breaking is desired, force can be applied to break the tablet at or about the separation mark in a direction that is substantially perpendicular to the surface on which it is desired that breakage of the tablet will be initiated. The tablet according to the invention may be broken either by applying force manually or by an instrument such as a cutting edge directly to the separation mark, or to other areas of the tablet, such as the outer segments, to cause the tablet to break at or about the separation mark and in the direction of the separation mark.

The separation mark or marks may comprise one or more of the following:
(a) a score in a side wherein said score is not oriented vertically;
(b) indicia on at least one side or lateral face of the tablet that indicates or locates a desired breaking region of said tablet;
(c) a band which is located on one segment or at an interface of two segments; or
(d) an inner segment of said tablet in which a first lower and a second upper segment have the same color and contain either the same drug in a pharmacologically effective quantity or both lack a pharmacologically effective quantity of any drug, and the third, inner or interposed segment that has a different color from said first segment and has either the same drug as said first segment when said first segment has a pharmacologically effective quantity of a drug or has no pharmacologically effective quantity of a drug when said first segment lacks a pharmacologically effective quantity of any drug.

Examples of specific embodiments of the invention are best described with reference to the drawings. The drawings depict vertical cross-sectional views of tablets and tablettes of the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die before they were separated from the intact tablet. Shaded areas represent segments derived from active granulations, i.e., those which contain a drug; clear (plain) areas, represent segments derived from inactive granulations, i.e., those formulated with no active drug.

Figure 2D:
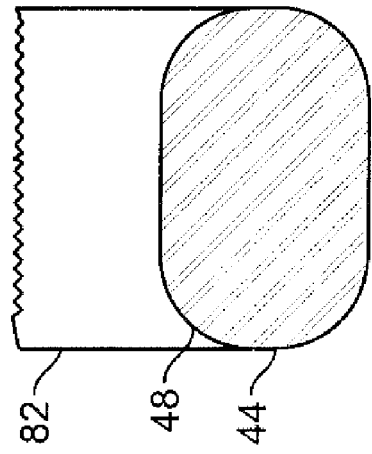

"Front views" refer to a cross-sectional view of a tablet that has a theoretical geometric plane passed through the tablet relative to a side which is arbitrarily designated, as the front. Figures labeled as "side view", which also have a corresponding "front view", are taken as a cross-section through the whole tablet: from the right side of a front view i.e. a side view is a cross-section that is taken by passing a plane through the vertical axis of the whole tablet at a 90° angle to the cross-sectional front view. Each front view represents a schematic cross-section that passes through the midpoint of the horizontal cross-section as measured from, the front of the tablet to the back of the tablet or tablette. The front view is also parallel to the major axis of the tablet (e.g, for a tablet with a rectangular (but not square) transverse cross-section, the longer side of the perimeter is parallel with the plane that depicts the cross-sectional, front view). That plane is located half-way between the front, and back, surfaces of said tablet. The side views of FIGS. 1b and 2c-d are taken from a vertically-oriented plane that passes through the midpoint of the longer transverse dimension (i.e., the width), and thus are located at and perpendicular to the mid-point of the front view. Drawings are of tablets that, have a rectangular but not square horizontal cross-section at the vertical mid-point of the tablet.

Segments containing pharmacologically active amounts of a drug or drugs are shown crosshatched; pharmacologically ineffective segments are shown plain (clear, without crosshatching or stippling). For consistency, tablettes are depicted in the same orientation as the tablets from, which they are formed, although tablettes are created after tablet ejection from the die. Dotted lines in the tablets depicted in the figures may represent printed marks or other indicia, or scores that are present on or in the surface of the tablet and, if they represent a score, said score does not extend deeply enough into the tablet to appear in the cross-sectional front view. The transverse dotted lines reflecting scores shown in the figures imply no intention to limit the depth of any scores of the tablets of the invention. Horizontal dotted lines on the front views that represent the surface scores are schematic, and do not necessarily represent the full vertical extent of a score, printed mark, or the like.

Tablettes are depicted with broken surfaces as indicated by a saw-tooth pattern. Such saw-tooth depiction is schematic and not intended to represent the actual pattern of breaking of a tablet (or tablette), which often leads to irregular edges even if said tablet is broken through a score.

Separation marks in the tablets depicted in the Figures are depicted as scores that are present on or in the surface of the tablet and that do not extend deeply enough into the tablet to appear in the cross-sectional front views are depicted in the drawings as dotted lines to reflect the location of said scores on or in the surface of the tablet (not shown). It is to be understood that the depth of a separation mark or other score may be deeper than one-half the widest cross-section of the tablet in a particular embodiment, and thus the transverse dotted lines reflecting scores that are separation marks shown in the Figures imply no intention to limit the depth of any scores of the tablets of the invention. Similarly, the tablets shown that contain scores do not limit the width or extent of said scores. The horizontal dotted lines on the front views that represent the surface scores are schematic, and do not necessarily represent the full vertical extent of the score. (Perforations or discontinuous scores through the width or depth of the tablets are not depicted herein, but remain within the scope of the invention, as are other marks on or physical changes to the tablet that create a separation mark.) Any scores or printed indicia that serve as separation marks are for convenience herein assumed to be on the front surface of the tablet, which is arbitrarily chosen from a vertically-oriented surface of the tablets. The "side view" of a tablet is a cross-sectional view of the tablet rotated 90 degrees from the front view, and is shown in FIG. 2c and 2d. No dimension of the separation marks is limited by their depiction as dotted lines in any figure.

Tablets of the invention are described herein in more detail than above. All segments that substantially lack drug activity are intrinsically of immediate release nature. The tablets are therefore of altered release or controlled release nature due to the composition of the one or more segments that: is or are intentionally formulated to have such a quality.

FIGS. 1a and 1b depict a tablet with compositionally substantially identical upper segment 40 and lower segment 44. In a preferred embodiment, a controlled-release formulation of a metoprolol salt is present in each segment inner segment 42 contains trace amounts of the drug that is present in a therapeutically effective quantity in each of segments 40 and 44; in a preferred, embodiment said drug comprises coated particles of metoprolol. Interfaces 46 and 48 represent regions in which the upper part of segment 42 and the lower part of segment 42 respectively adjoin upper segment 40 and lower segment 44. The curved interfaces result from the profile, of the upper tablet punch which is curved. Score 52 is depicted in FIG. 1*b*. Dotted line 50 in FIG. 1*a* is a reflection of score 52 on the surface of the tablet (not shown), that does not penetrate half-way through the shorter transverse axis of the tablet.

FIGS. 2*a*-*d* depict tablettes formed from breaking the tablet of FIGS. 1*a* and 1*b* through score 52. Inner segment 42 of FIG. 1*a* no longer exists as an intact segment. The upper tablette of FIGS. 1*a* and 1*c* contains segment 80 that adjoins intact upper segment 40 and the lower tablette contains segment 82 and intact segment 44.

Breaking the tablet of FIGS. 1*a* and 1*b* through the score placed in segment 42 is clearly easier than breaking the tablet through its vertical dimension, which is currently the practice with scored layered (segmented) tablets, though it should be noted that the current and limited practice of scored layered tablets involves, probably exclusively, tablets that are taller than they are wide. The fact, that during preferred means of breaking said tablet, no break is made in the parts of the tablet where the active drug has been placed provides for exceptionally accurate breaking relative to the active drug or drugs contained in the tablet.

Figure 3:
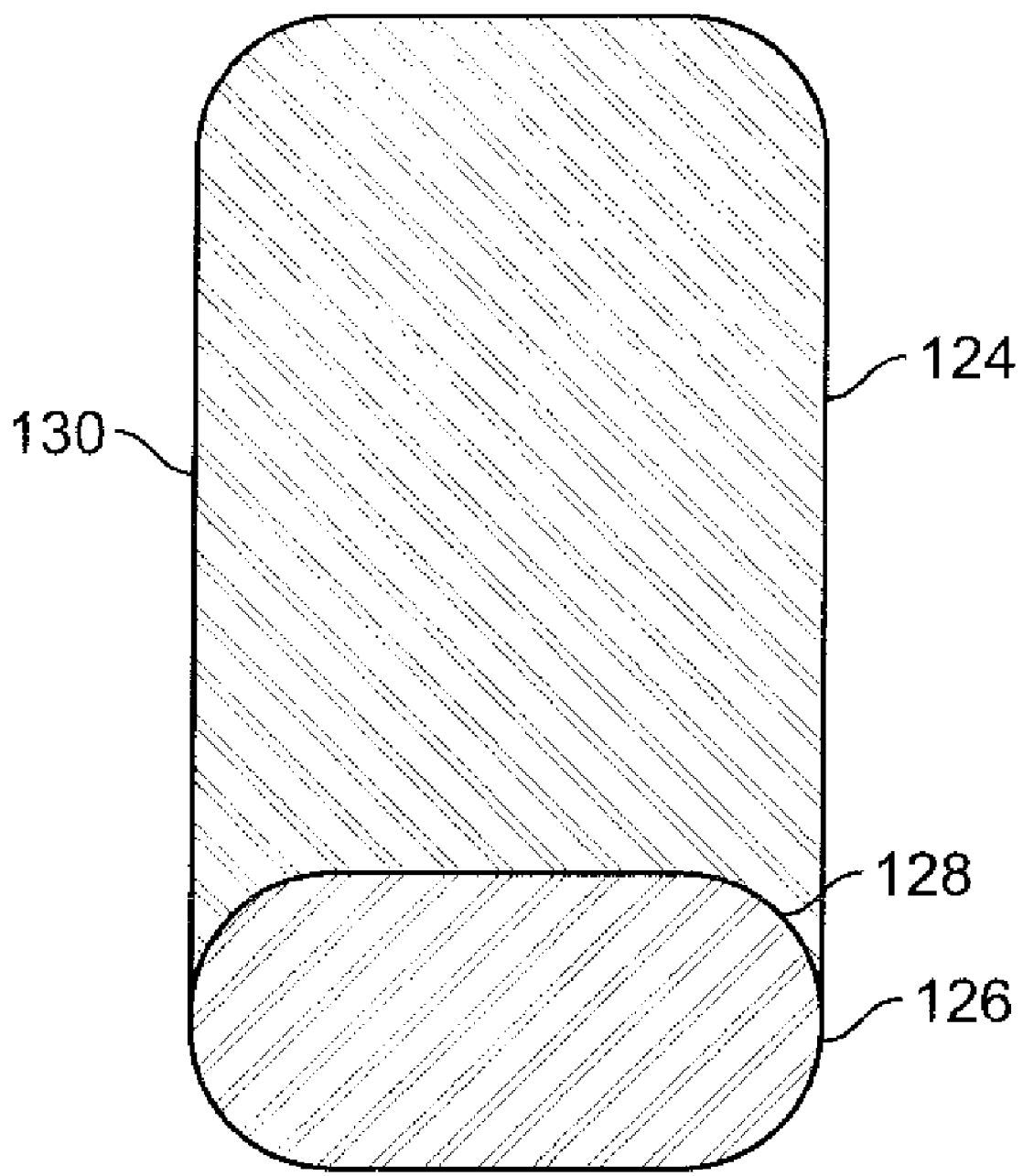
FIG. 3 is a cross-section of a taller than wide tablet having two segments, one of which is about three-quarters of the height of the tablet.

FIG. 3 demonstrates a two-segment tablet, each segment formed from a granulation containing a pharmacologically effective amount of medication. In a preferred embodiment, coated particles of verapamil that create a controlled release of said drug comprise upper segment 124 and an immediate release granulation of verapamil comprises lower segment 126. Upper (outer) segment 124 is larger than lower (outer) segment 126. Interface 128 indicates a region (interface) at which said segments are contiguous. A printed mark on the outer surface of the tablet (not shown) indicates a potential breaking point, as indicated by the location of arrow 130 that reflects the position of said surface printed mark. The two segments 124 and 126 also have different colors; however, further allowing identification of which part of the tablet contains which segment.

Figure 4A:
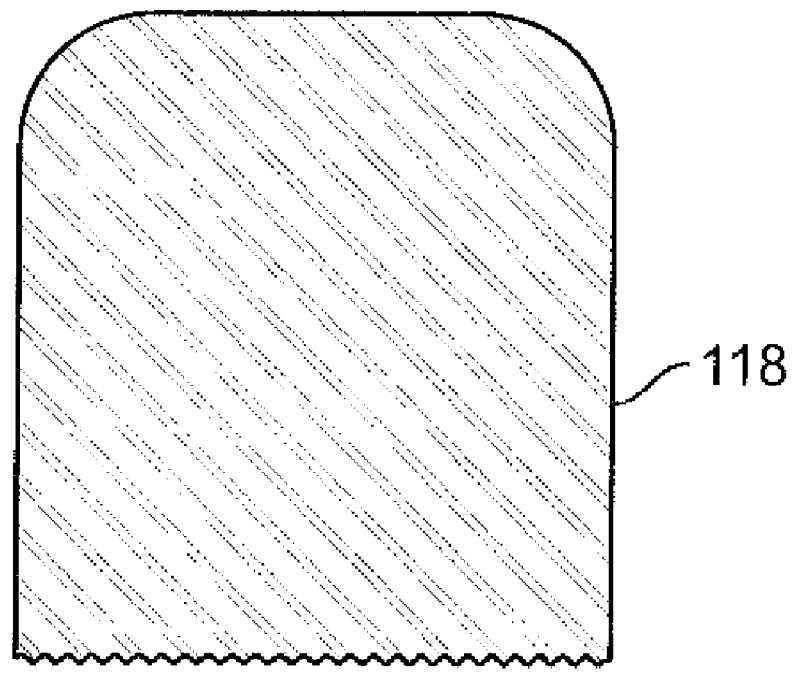
FIGS. 4a-b are views of FIG. 3 when the tablet has been broken transversely.
Figure 4B:
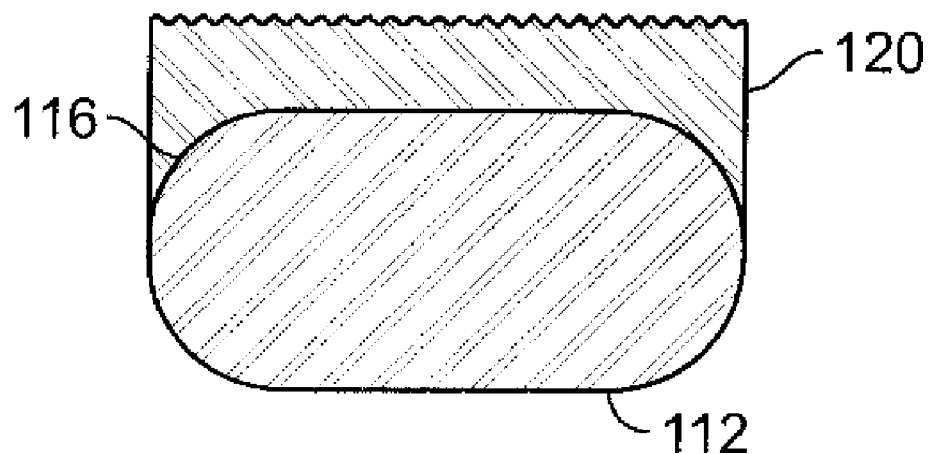

FIGS. 4*a* and 4*b* depict the two tablettes formed by breaking the tablet of FIG. 3 though not as directed by print mark as indicated by arrow 130. The tablette of FIG. 4*a* consists of segment 118, which represents the bulk of segment 124 of FIG. 3. The tablette depicted in FIG. 4*b* contains segment 112 in an intact form and segment 120, which represents a less than half-portion of segment 124 of FIG. 3. Interface 116 indicates a region at which said segments are contiguous. The curvature of interface 116 is due to the profile of the upper tablet punch.

Figure 5:
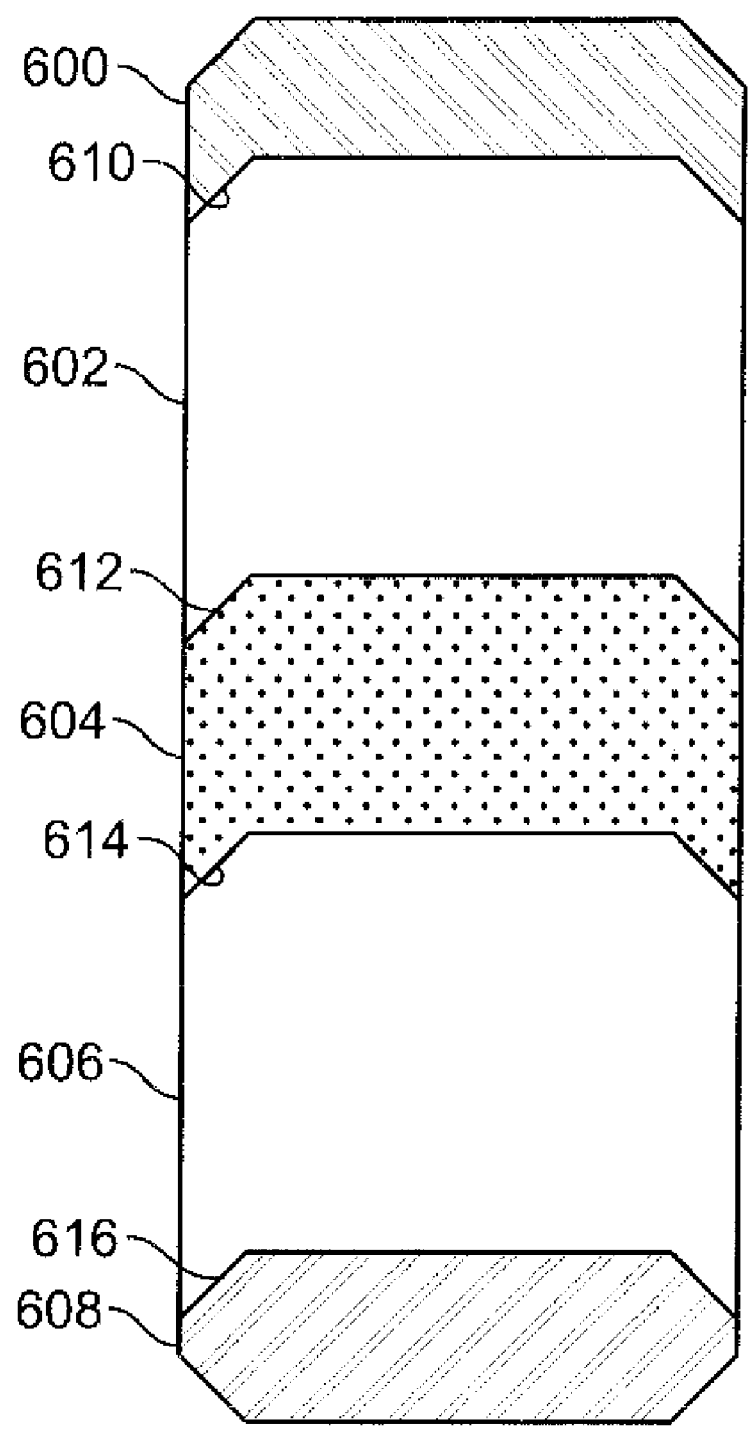
FIG. 5 is a cross-section of a taller than wide tablet having five segments.
Figure 6A:
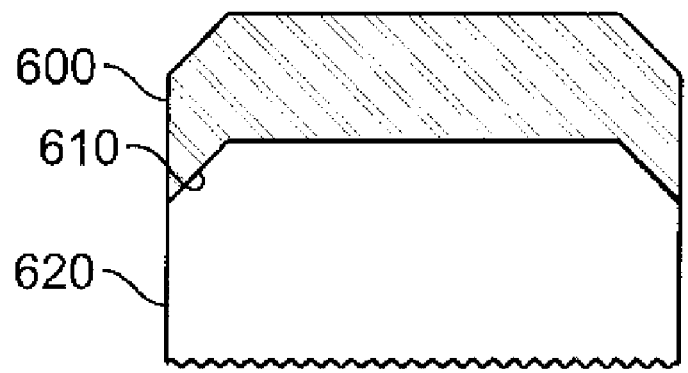
FIGS. 6a-b are views of FIG. 5 when the tablet has been broken through one segment.
Figure 6B:
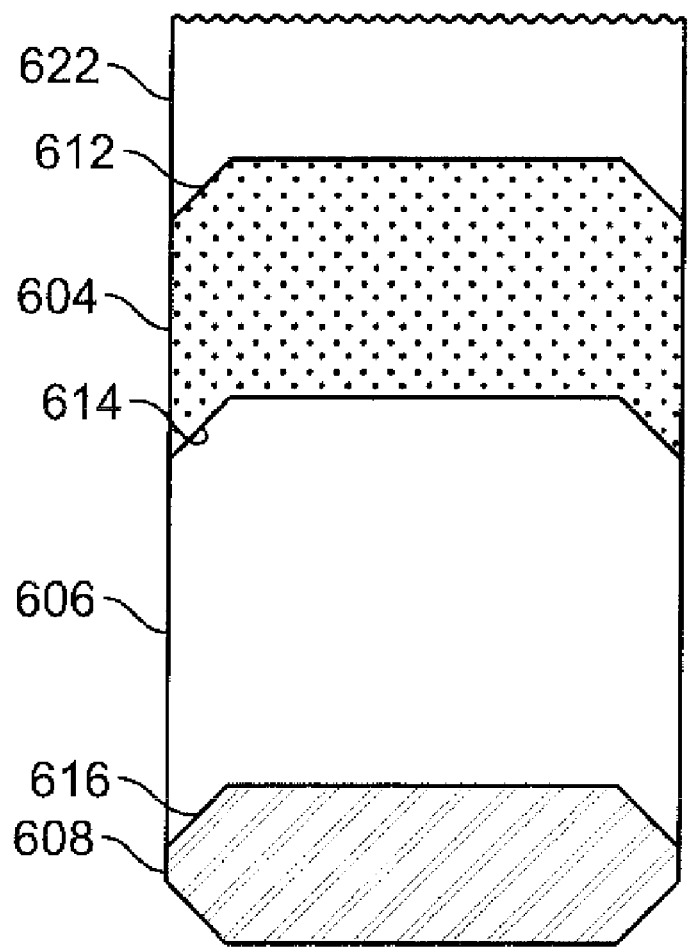

FIG. 5 illustrates a tablet more elongated than those previously demonstrated. Said tablet is adapted, even more than the others, for ease of breaking through one segment. Upper segment 600 is provided with a therapeutic quantity of a drug; stippled inner segment 604 is provided with a therapeutic quantity of a different drug; and, lower segment 608 is provided with, a therapeutic quantity of a drug different from that found in a therapeutic quantity in segments 600 and 604. Clear (plain) inner segments 602 and 606 contain pharmacologically ineffective amounts of each of the three drugs found in the tablet, though in less preferred embodiments, inadvertent mixing of the three different granulations is sufficient to produce a pharmacologically effective though not therapeutically effective dose of a drug or drugs. In yet a different embodiment, segment 604 is provided with a therapeutic quantity of a vitamin such as folic acid; and in addition, in a less preferred embodiment, segment 606 may also be provided with a therapeutic, quantity of a drug as well. Interfaces 610, 612, 614, and 616 represent the regions at which two contiguous segments adjoin. The tablet of FIG. 5 is provided with a different color for each segment, though no requirement for this color differentiation by segment exists for tablets of the invention. Even though there is no surface scoring or indicia, the color scheme is such that a person's attention may be directed to apply force to break the tablet, through segment 602 to create the tablettes depicted in FIGS. 6*a* and 6*b*. FIG. 6*a* depicts the smaller tablette created by breaking the tablet of FIG. 5 through segment 602 in a transverse fashion. Segment 620 has been created by said breaking, and segment 602 of FIG. 5 no longer exists as an intact, segment. FIG. 6*b* depicts the larger tablette created by said breaking of the tablet of FIG. 5. New upper segment 622 has been created.

Segment 608 of the tablet of FIG. 5 comprises an altered-release pharmaceutical agent chosen from those well known in the art. No limitation of the ratios of the five segments of said tablet relative to the dimensions of the whole tablet exists.

Figure 7A:
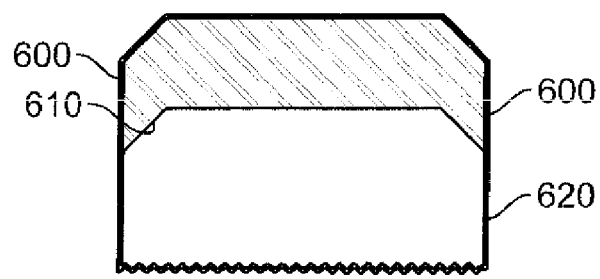
FIGS. 7a-c are views of FIG. 5 when the tablet has effectively been broken through two segments in two steps, first by breaking the tablet and then by breaking the tablette of FIG. 6b.
Figure 7B:
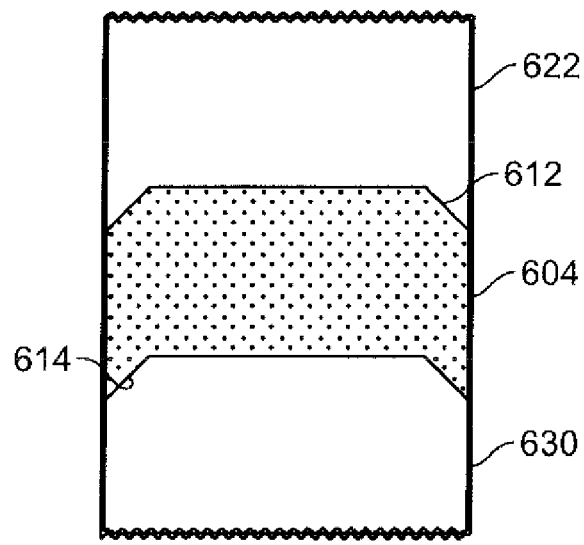
Figure 7C:
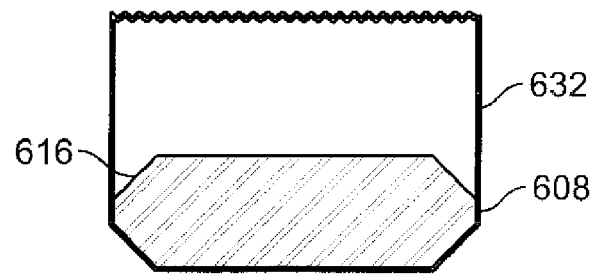

FIGS. 7*a*-*c* depict three tablettes created, by the subsequent breaking of the tablette of FIG. 6*b*. New segment 630 and segment 632 have been created, and segment 606 no longer exists as an intact segment. Assuming minimal to no intermixing between the materials forming each segment of the tablet of FIG. 5 and assuming that segment 632 of FIG. 7*c* is substantially free of any active drug, the tablette of FIG. 7*c* represents a novel altered release dosage form, in part, in that it consists of an altered release product adjoining in a segment an immediate release substantially inactive segment.

Figure 8:
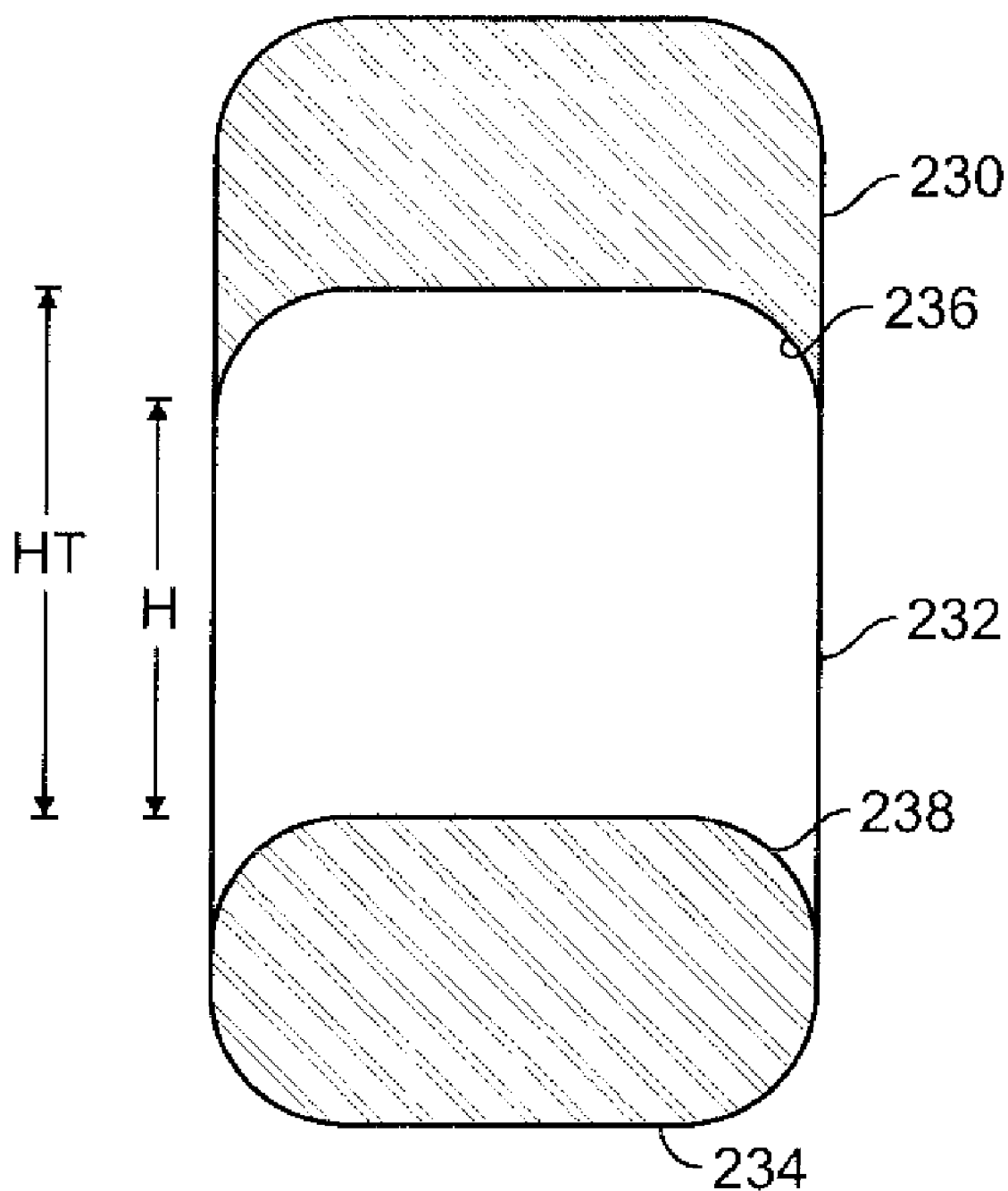
FIG. 8 is a cross-section of a tablet that has three segments.

FIG. 8 is a cross-section view of a tablet with three segments.

Figure 9:
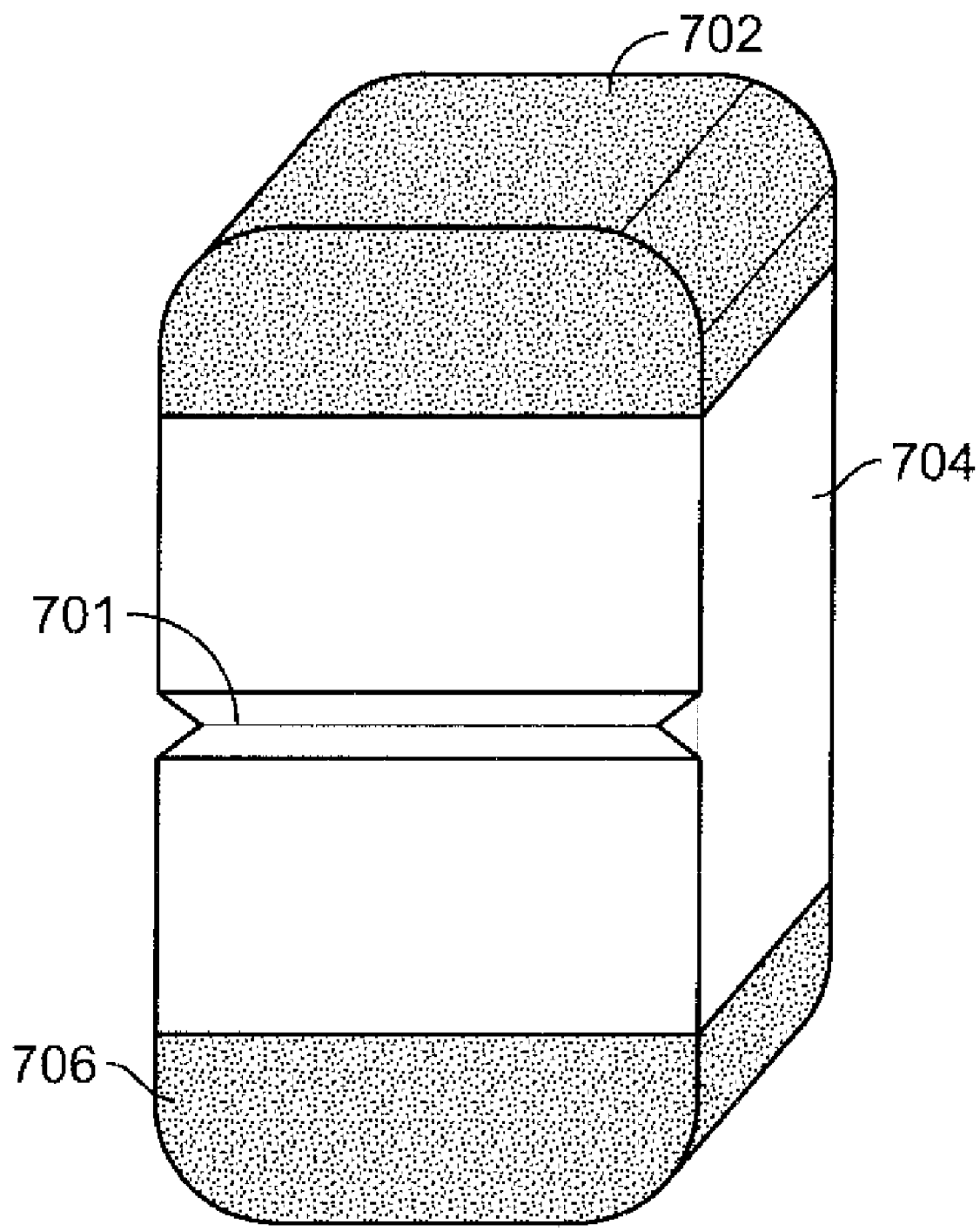
FIG. 9 is an external perspective view of a scored tablet that has three segments.

FIG. 9 is a perspective view of a tablet of the invention which shows score 701 as a separating mark on a front surface and top active (drug-containing) segment 702; middle pharmacologically inactive segment 704 (no pharmacologically effective amount of a drug) and bottom active segment 706. When the tablet is broken through the score 701, the top segment and the bottom segment will remain intact. Segments 702 and 706 each contain a compositionally identical controlled release beaded formulation of verapamil plus immediate-release hydrochlorothiazide ("HCTZ"). Pharmaceutically ineffective quantities of verapamil and HCTZ are found in segment 704.

Figure 10:
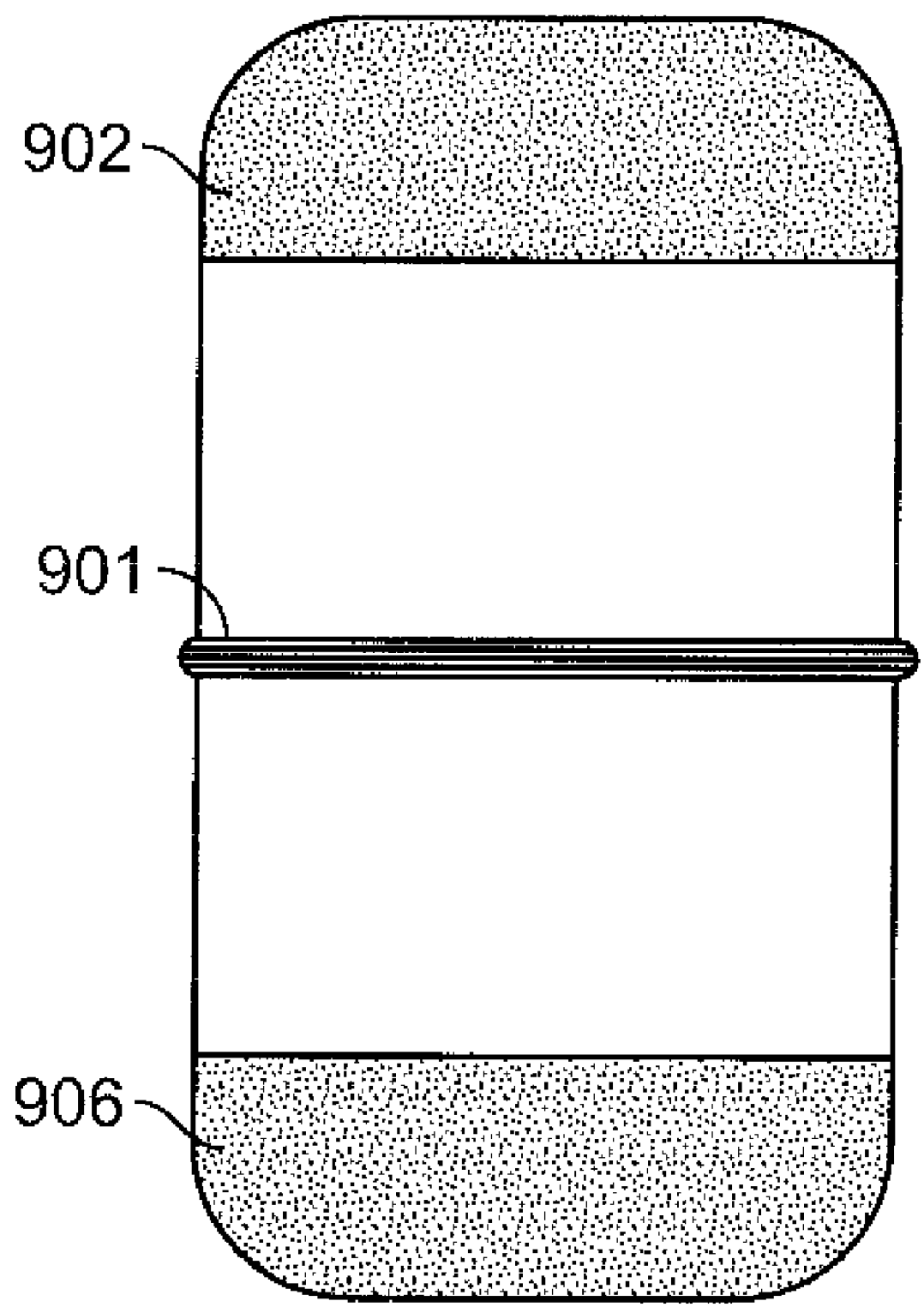
FIG. 10 is an external en face view of a tablet that has three segments and that has a band around the width of the middle (inner) segment of the tablet that extends to the sides.

FIG. 10 is a front view of a tablet of the invention showing a gelatin band 901. Techniques such as those used to band capsules, as disclosed in U.S. Pat. No. 4,922,682, which is incorporated by reference, may be modified to provide a band in making tablets according to the invention. Segments 902 and 906 are compositionally distinct and contain different volumes of material. Lower segment 906 comprises potassium chloride in a matrix formulation; upper segment 902 comprises an immediate-release composition of chlorthalidone. Middle (inner) segment 903 contains small amounts of chlorthalidone but not in a pharmaceutically effective quantity.

Figure 11:
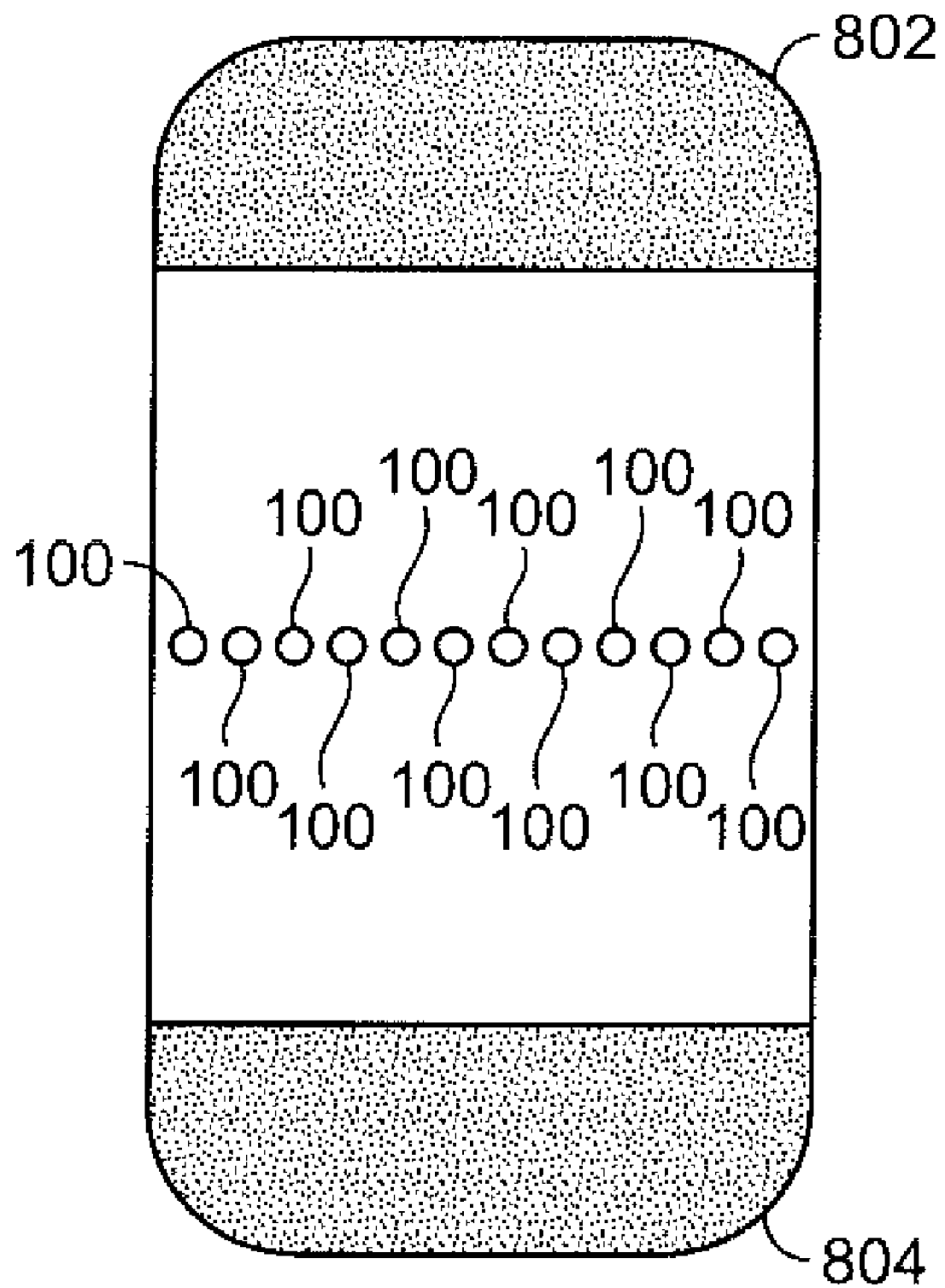
FIG. 11 is an external en face view of a tablet that has three segments into which perforations have been created in the middle segment.

FIG. 11 shows a series of perforations 100 that may be made in the surface of a tablet to form a separation mark according to the invention. These perforations may be formed e.g. by mechanical or laser drilling 1-2 mm diameter holes that, extend into the surface to a depth of 1-2 mm. The stippled upper and lower segments 802 and 804 contain a modified, release preparation of pentoxyphylline. Un-numbered middle segment containing perforations 100 comprises inactive excipients.

Figure 12:
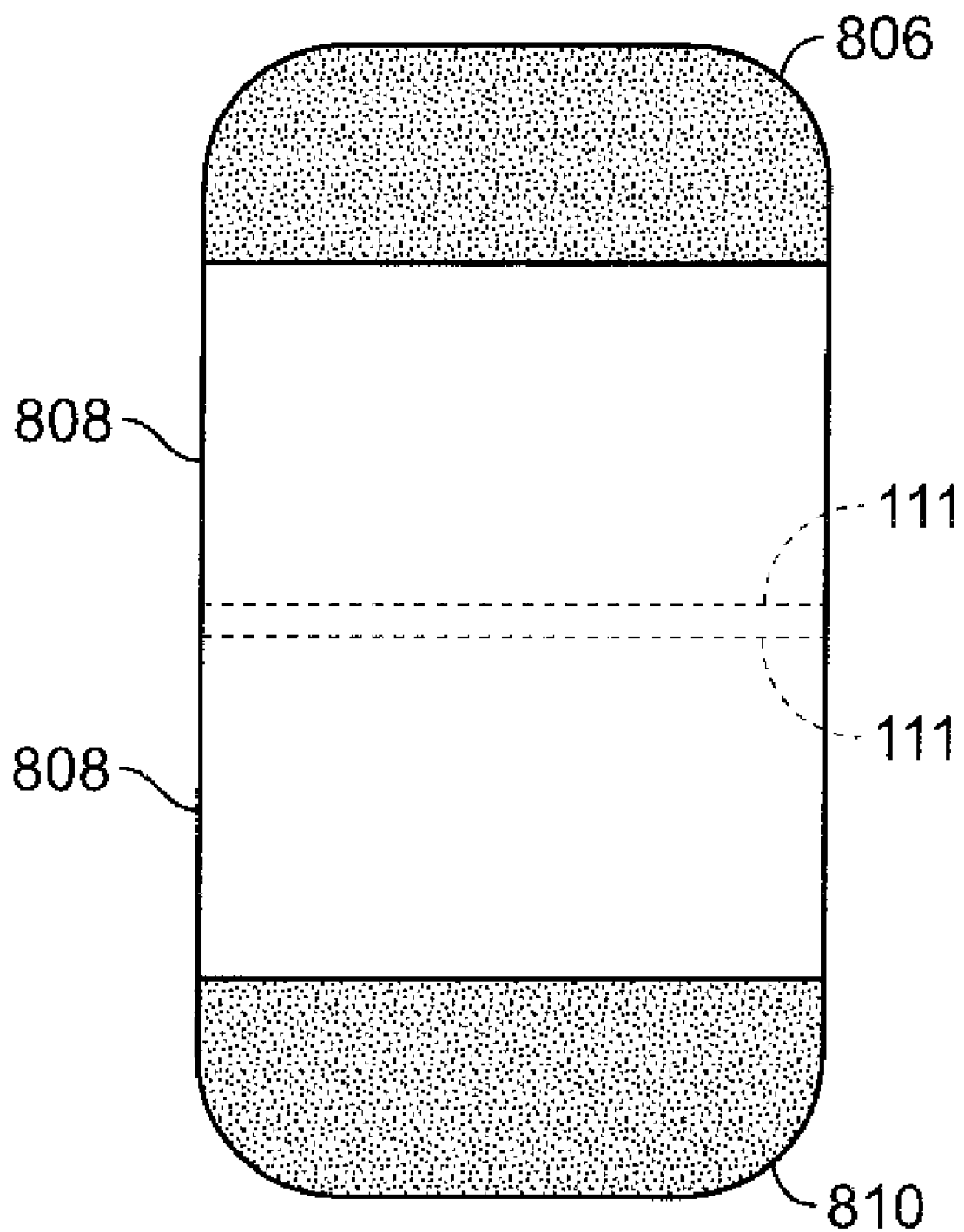
FIG. 12 is an external view of a tablet with three segments on the middle segment of which are two horizontal (transverse) dotted lines close together.

FIG. 12 shows a front view of a tablet according to the invention that has two printed dotted lines that serve as a separation mark according to the invention. Middle segment 808 comprises a therapeutically effective quantity of folic acid and vitamin B12. Lower segment 810 comprises controlled release beads of a metoprolol salt in a therapeutic quantity and upper segment 806 comprises a therapeutic quantity of amlodipine. Sub-therapeutic quantities of the following drugs are found in the following segments: for and vitamin B12 in segments 806 and 810, metoprolol in segments 806 and 808, and amlodipine in 808 and 810.

Figure 13:
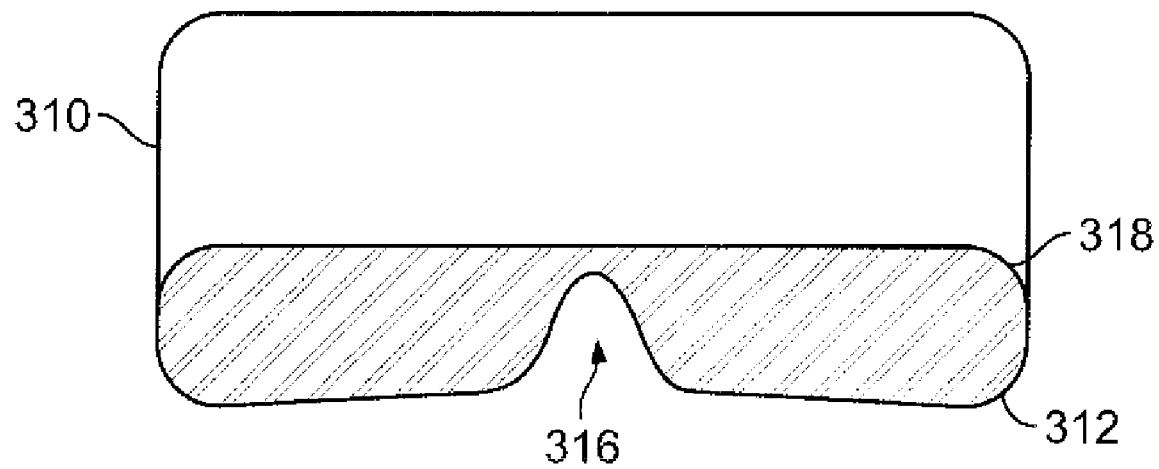
FIG. 13 is a cross-section of a wider than tall tablet with two segments one of which is deeply scored.

FIG. 13 depicts an immediate release tablet with a score 316 that extends approximately 90% through the bottom segment 312. Upper segment 310 allows structural stability of the tablet despite the deep score 316. In this tablet, no pharmacologically effective dose of the drug present in segment 312 is present in segment 310. In another preferred embodiment, segment 310 may contain a different drug than is present in segment 312, preferably in a pharmacologically effective quantity. In a less preferred embodiment, segment 310 contains a pharmacologically effective quantity of the drug or drugs present in segment 312, but in a diminished concentration relative to the excipients in each segment. Interface 318 is present. In this tablet, an active drug in a composition with altered release characteristics is present in a therapeutic quantity in segment 312, and segment 310 lacks a therapeutic quantity of the same or any other drug. The novelty of the tablet design would remain, however, were segment 310 to be provided with drugs such as a pharmaceutically effective or therapeutically effective quantity of a different drug. Novelty would also be present, for example, if the altered release composition were present in a therapeutically effective quantity in unscored segment 310 and a therapeutically effective quantity of a different immediate release composition of a drug were present in scored segment 316.

Figure 2A:
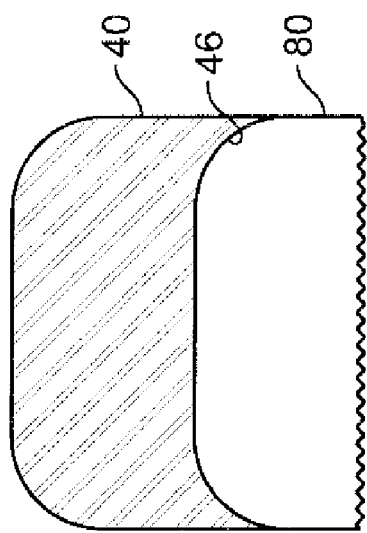
Figure 2B:
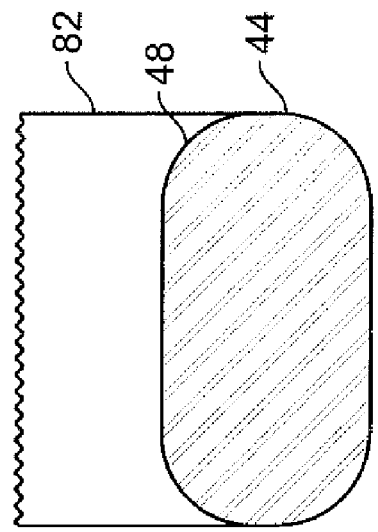

Breaking the tablet of FIG. 13 may give two tablettes as shown in FIGS. 14a and 14b, though no limitation as to the direction of tablet breaking is intended. Largely inactive segment 310 of FIG. 1 has been divided into two segments, 700 in the smaller tablette as shown in FIGS. 2a and 702 in the larger tablette of FIG. 2b. Even though breaking as demonstrated is far from vertical, it is clear that the amount of drug in new segments 314 and 315 created from segment 312 of FIG. 1 is similar. Two new segments, 706 in FIGS. 2b and 704 in FIG. 2a, are created by said creation of the two tablettes. New interfaces 708 and, 710 lie at the regions at which segments 702 and 706, and 700 and 704, respectively, adjoin.

Figure 15:
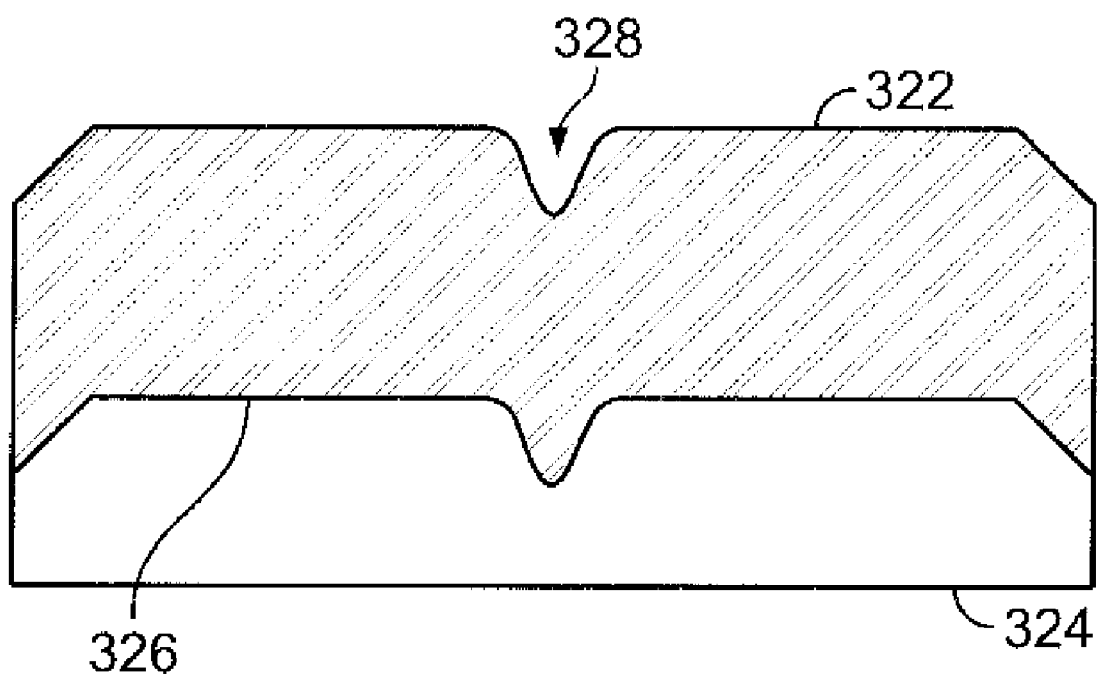
FIG. 15 is a cross-section of a tablet with two segments one of which is substantially inactive.

FIG. 15 depicts a two-segment tablet. In this tablet, lower (bottom) segment 324 contains a drug different from that contained in upper (top) part 322. Score 328 indents segment 324. Interface 326 is present at the region at which segments 322 and 324 meet. The tablet of FIG. 8 is not a taller than wide tablet. FIG. 8 depicts a schematic of a tablet of the prior art of bilayer tablets. One may readily appreciate the difficulty inherent in attempting to break a tablet such as the tablet of FIG. 8 horizontally, through one segment only, or, analogously, a tablet similar to that of FIG. 8 but that in addition was provided with, say, a segment below that of segment 324.

Figure 16:
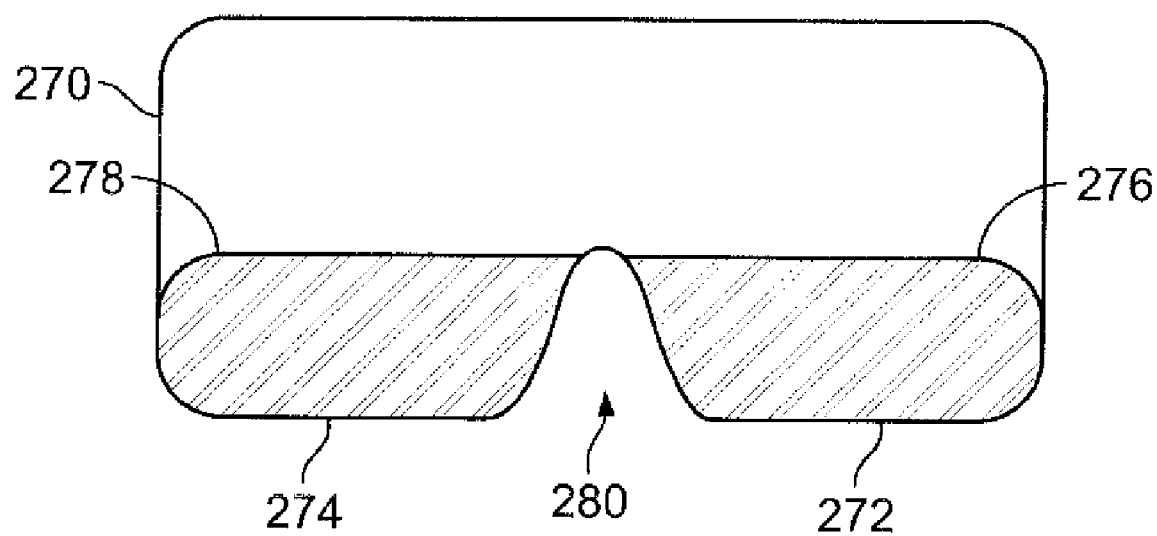
FIG. 16 is a cross-sectional view of a three segment tablet, two segments of which are unitary segments.

FIG. 16 depicts a tablet containing unitary segments 272 and 274 in vertical cross-section, front view. Both of said unitary segments adjoin the same face (surface) of segment 270, which is formed from a single granulation and due to mixing of granulations, contains a minimal amount of the drug that is present in segments 272 and 274. Interfaces 276 and 278 represent the regions at which segment 270 adjoins segments 272 and 274, respectively. Score 280 indents segment 270 and also represents the space between segments 272 and 274. Unitary segments 272 and 274 contain an altered release composition of a pharmaceutical. Segment 270 is formed from inactive excipients that do not affect the release rate of said pharmaceutical from the tablet.

FIGS. 17a and 17b depict the two tablettes created by breaking the tablet of FIG. 16 through segment 270. In FIG. 17a, segment 302 represents that part of segment 270 that adjoins intact segment 274. Interface 278 represents the region at which segments 302 and 274 meet. In FIG. 17b, interface 276 represents the region at which segments 304 and 272 meet. Score 280 and segment 270 of FIG. 16 are not considered to exist once the tablettes are formed. Each tablette of FIGS. 17a and 17b contains substantially equivalent mass assuming the score 280 of FIG. 16 is a bisecting score relative to the layer that became divided in the creation of segments 272 and 274.

Tablets of the nature of that of FIG. 16 may contain in the unitary segments a mixture of drugs or, as in FIG. 1, one drug. In addition, the granulation that forms segment 270 of FIG. 16 may be provided with a drug that is the same as, or different than, that of the divided layer. In such a case, it would be preferable that said drug provided in the upper layer (segment) would have a therapeutic effect and side effect profile that was not very sensitive to accuracy of subdivision of a dose.

In addition, no limitation exists as to the presence of one or more additional segments created superior to (i.e., above) segment 270, or the composition of such. Also, though less likely, there could be another set of different unitary segments inferior to (i.e., below) segments 272 and 274.

Figure 18:
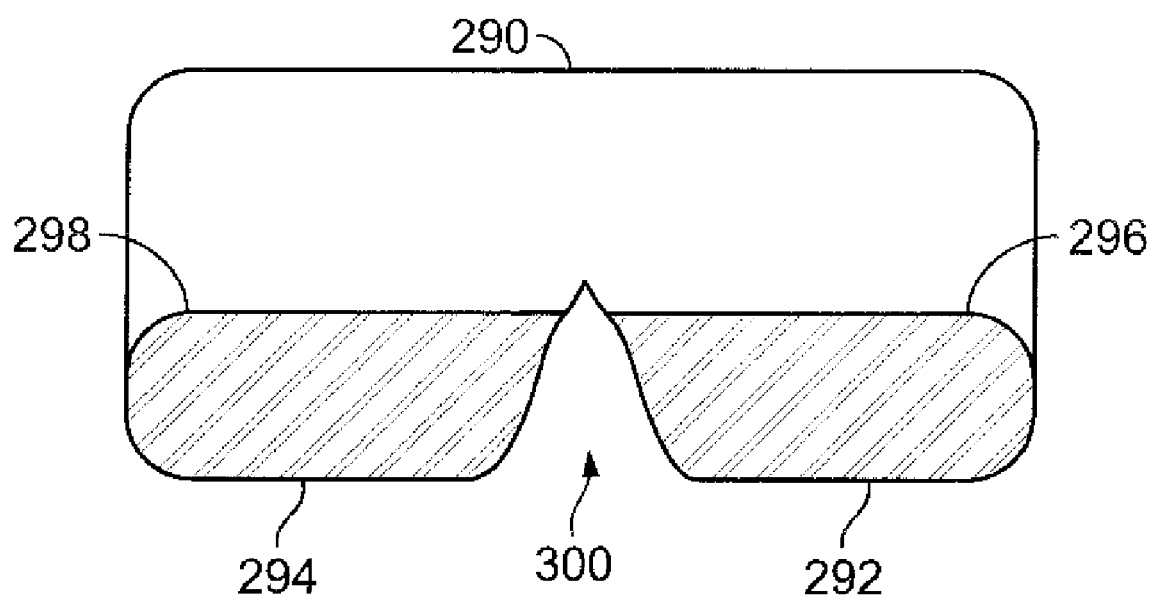
FIG. 18 is a cross-section view of a tablet with three segments, two of which are unitary segments.

FIG. 18 depicts a tablet in a cross-sectional view that is similar to that depicted in FIG. 13, but the tablet of FIG. 18 has a score 300 that extends more deeply into the non-unitary segment 290 than does score 280 of FIG. 13. A preferred method of producing score 300 is to use the embossing and manufacturing technique used for the tablet of FIG. 13 and then remove, such as with a file, material from segment 290. Alternatively, embossing of the appropriate size and shape may be able to be utilized to create score 300 directly. The tablet of FIG. 18 contains unitary segments 292 and 294. Interfaces 29G and 298 are present between segments 292 and 290, and 294 and 290, respectively.

Figure 19A:
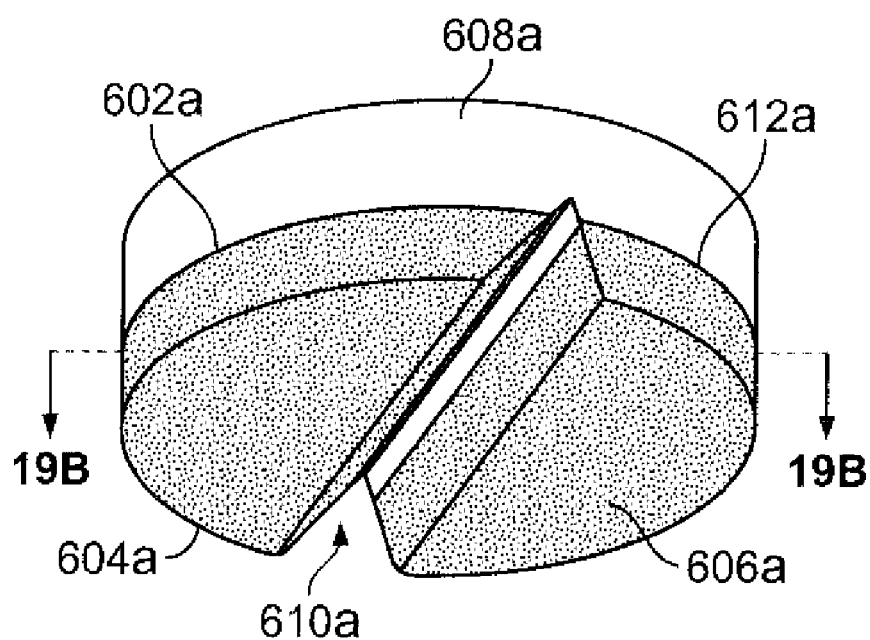
FIG. 19a is a external perspective view of a three segment tablet with two unitary segments.

FIG. 19a depicts an external view of a tablet containing unitary segments 604a and 606a that are at the bottom of the tablet. In this tablet, score 610a penetrates into clear, upper, non-unitary segment 608a. Interface 602a represents the region at which segment 608 meets segment 604a. Interface 612a represents the region at which segment 606a meets segment 608a.

Figure 19B:
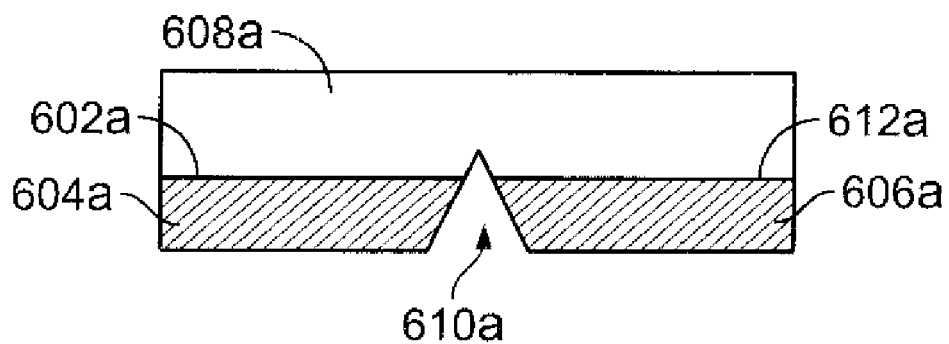

FIG. 19b depicts the same tablet depicted in FIG. 19a. This vertical cross-section is taken perpendicularly through score 610a, which occupies the diameter of the circular transverse cross-section of the tablet. The unitary segments of the tablets of FIGS. 19a and 19b comprises therapeutic quantities of diltiazem in beads producing controlled release of diltiazem to last twelve hours at least in therapeutic effect. Segment 608a has no therapeutically effective quantity of any drug.

Figure 20:
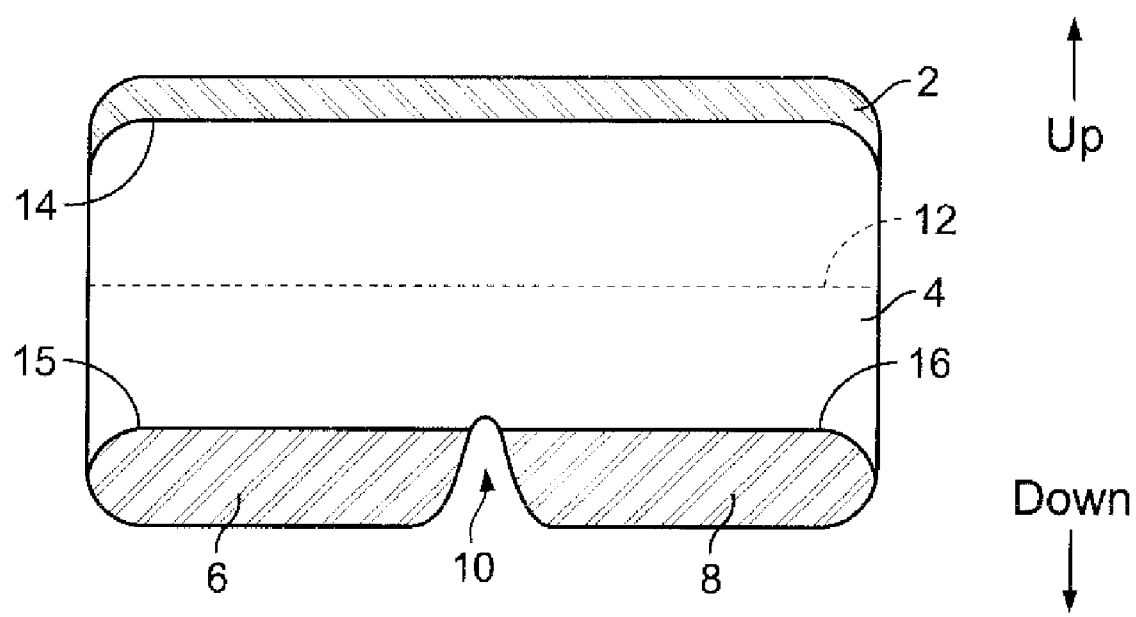
FIG. 20 shows a tablet with four segments, two of which are unitary segments.

FIG. 20 depicts a tablet containing four segments. Unitary segments 6 and 8, as with all unitary segments, are not contiguous with each other. Score 10 penetrates into segment 4. Segment 4 is a compound segment formed from substantially compositionally identical inactive granulations added sequentially with immediate release characteristics. Top segment 2 contains a therapeutic quantity of a drug that differs from the drug that is present, in a therapeutic quantity in segments 6 and 8. Dotted line 12 reflects a surface score that runs transversely across segment 4. A preferred horizontal dimension for the tablet of FIG. 20 is 12-18 mm, but said dimension is not limited. Interface 14 depicts where segments 2 and 4 are contiguous. Interfaces 15 and 16 depict where segments 6 and 8, respectively, adjoin segment 4. Segment 4 contains therapeutically insignificant quantities of the drugs found in segments 6 and 2. The tablet of FIG. 20 may be broken usefully in two ways. One way is vertically through score 10 in the direction of segment 2; such breaking would not utilize the score reflected by dotted line 12, but would give a dose of half of the drug found in segments 6 and 8, though likely would not give a precise halving of the drug found in segment 2, due to difficulties with breaking scored tablets as was documented in the Background of the invention, above. The result of another way of breaking said tablet is depicted, schematically in FIGS. 21a and 21b.

The relative dimensions of segments in the tablet of FIG. 20 are not limited. In said tablet, an immediate release formulation of candesartan is present in the top segment, the middle segment lacks pharmacologic activity, and the unitary segments comprise sustained-release metoprolol.

Figure 21A:
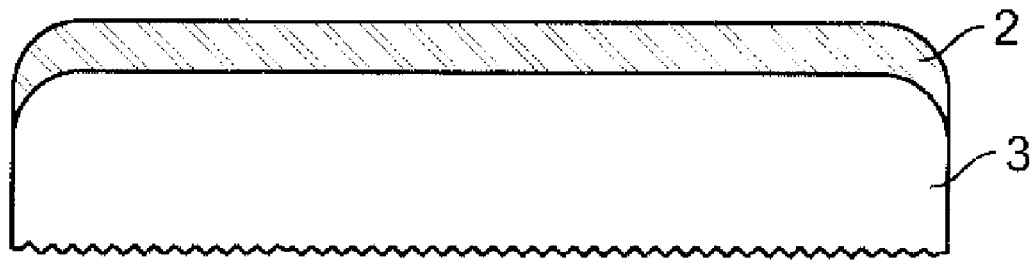
FIGS. 21a and 21b are cross-sections of each tablette formed by breaking the tablet of FIG. 20 through the middle segment.
Figure 21B:
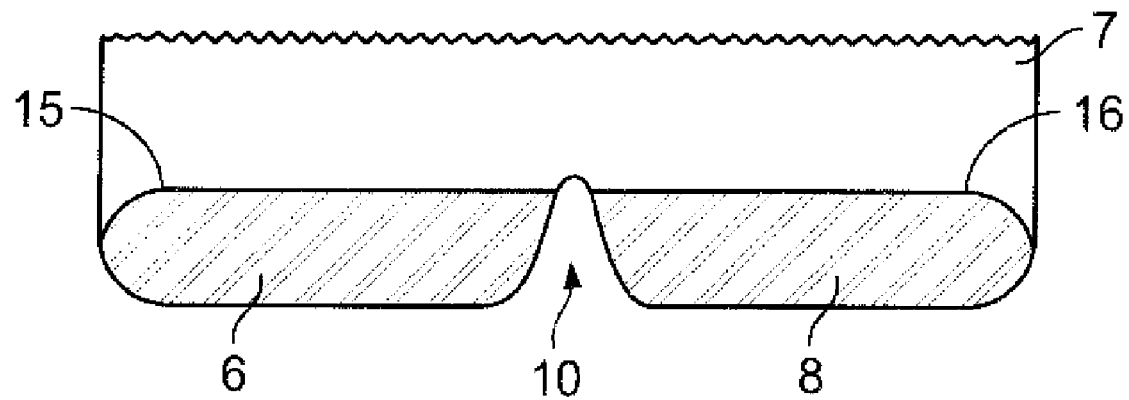

FIG. 21a shows a tablette formed from breaking the tablet, of FIG. 5 through the horizontal score reflected by dotted line 12. As with other tablettes depicted herein, it is not assumed that breaking is even, but the tablettes are depicted so that, breaking is contained substantially within segment 12, that, is a segment interposed between upper segment 2 and lower segments 6 and 8 in the tablet of FIG. 5. The tablette of FIG. 21a demonstrates that segment 2 is intact, as is interface 14. Segment 3 is formed by the part of therapeutically inactive segment 4 of the tablet of FIG. 5 that remains contiguous with segment 2. The tablette of FIG. 21b depicts segments 6 and 8, and interfaces 15 and 16, as unchanged from the tablet of FIG. 3. Segment 7 is the part of segment 4 of FIG. 5 that becomes part of the tablette of FIG. 6b.

A wider than tall tablet with, a relatively large inactive middle segment as depicted in FIG. 20 demonstrates that the invention of a tablet with a breakable inactive segment does not require that the tablet be taller than it is wide.

In addition, an external bottom view looking up at the unitary segments of FIG. 20 or FIG. 21b is not shown but if shown could demonstrate that the invention of unitary segments could easily allow for trisecting or quadrisecting Another preferred embodiment of the invention utilizes a variation on the above, for example:

A first, granulation comprising hydrochlorothiazide (HCTZ) enters the die, followed by an inactive granulation entering the die twice, followed at the fourth and final filling station by a controlled release granulation comprising metoprolol (a beta-blocker). After final compression, a tablet consisting of three segments (formed from four layers) has been created. The simple segment formed from the first granulation is the bottom layer, the layers formed from inactive excipients are the two inner layers and together, after tablet formation, make up the middle (inner) compound segment, and the final granulation comprises the top layer, which after final compression is denoted the top segment, which is a simple segment as defined herein. Thus all dimensions and directions herein relate to the method of manufacture of the tablet. This preferably taller-than-wide tablet may contain some amount of HCTZ in the middle and top segments, and may contain some amount, of metoprolol in the middle and bottom segments.

After breaking the above extended release metoprolol/hydrochlorothiazide (HCTZ) tablet entirely through the middle segment, two tablettes are formed. One tablette contains primarily the full, therapeutically effective quantity of HCTZ and may contain some amount, preferably a trace amount, of metoprolol; the other contains primarily the full amount of metoprolol and may contain some amount, preferably a trace amount, of HCTZ, plus some quantity of said middle segment. Important therapeutic benefits in terms of dosage adjustment, side effect management, and the like are obtained from the above tablet design and optional ability to substantially completely create two individual dosage forms from the combination product.

As FIG. 8 demonstrates, cupping or beveling of the upper punch commonly causes the peripheral parts of any segment other than the lowest segment, to extend below the level of the central part, of that segment. In order to fully realize the benefit of a "separating segment" per the invention, it is optimal that a transverse plane be able to be placed between the lowest part of a superiorly disposed segment, and the highest part of an inferiorly disposed segment, with said plane passing between an interposed, preferably pharmacologically inactive segment. The vertical distance between the lowest part, of a superiorly disposed segment, and the highest part of an inferiorly disposed, segment is herein denoted the effective height H, which is less than the height HT of the middle segment in FIG. 8 due to cupping of the upper punch. Generally, that, measurement, will be from the vertical height, from the bottom of the tablet to the plane drawn horizontally from the periphery of the higher segment, due to the cupping or beveling of such a segment, and from the vertical height from the bottom of the tablet to the center of the lower segment.

The effective height in the case of beveling or cupping of segments, as easily reflected in the shape of the top of the tablet, is always less than the height of the separating or interposed segment through which breaking is intended to occur. The height of an interposed segment is the vertical distance from its highest point to the highest point of the contiguous superiorly disposed segment.

In the case of separating or interposed segments, prior art limits the height to approximately 1 mm for immediate release pharmaceutical tablets. The effective height H has been limited to less than that for immediate release pharmaceutical tablets.

Another embodiment of the subject invention comprises a bilayer tablet, and preferably comprising unitary segments. Production may involve first allowing a granulation containing active drug into a die that has an embossed lower punch, so that said granulation forms an undivided layer indented from below by said embossing. Said embossing is not limited in its pattern. After optional and preferred tamping, an inactive granulation enters the die and after optional pre-compression, a tablet is formed by final, full-force compression. This compression pushes the first, lower layer almost to the level of the uppermost aspect of the embossing, so that an especially deep score may be produced. Each granulation, after entry into the die, forms a layer. After final compression of the tablet, each layer may also be referred to as a segment of the tablet. Except for inadvertent mixing between granulations, the upper segment is inactive, so that tablet breaking may occur substantially through the inactive, segment, thus providing substantial improvement over existing methods of scoring tablets from the standpoint of accuracy of subdividing a dose. Less preferably, the second granulation could contain a diluted quantity of the active ingredient or ingredients comprising said first granulation. Such a maneuver would be useful if it were difficult to place adequate drug substance entirely within said first granulation.

Additional preferred embodiments flow from the tablet of FIG. 13. In the case in which there were a desire to provide additional active drug in a segment above the deeply scored segment, a trilayer design could be useful, given certain practical limitations regarding the height of embossings. In this example, a highly concentrated granulation of drug forms the first granulation, which is pushed as close to the top of the embossing as possible; a second, less concentrated (w/w %) granulation comprising the identical active ingredient enters the die, and a third, inactive granulation finally enters the die. After final compression, a tablet that is preferably very deeply scored with respect to the first segment has been created, and the middle segment, which will tend to break more accurately than the outer segment, improves the accuracy of said tablet breaking relative to a tablet of simpler design.

Another preferred embodiment related to the example provided by the tablet of FIG. 13 is as follows. A first active granulation enters the die onto an embossed lower punch and is tamped. A second, inactive granulation enters the die at the second filling station and again at the third filling station, and is optionally and preferably tamped after each of said granulations enters said die. At a fourth filling station, a different granulation from the first enters the die, is optionally and preferably tamped, and then final compression takes place, pushing said first granulation lower into the die so that the uppermost part of said first granulation remains above the uppermost part of said embossing. Thus, said first granulation has formed an undivided layer. In this example, the use of two identical granulations to form two layers that are compositionally substantially identical may be useful to form one tall segment. Such a segment, whether formed from two or more substantially identical inactive granulations or ones comprising an active drug or drugs, is called, a compound segment, herein. The utility of the dosage form is that, it allows different active drugs to primarily be placed in opposite ends of a "taller than wide" tablet, so that both drugs may be given together in a whole tablet, but said tablet also may be broken through a middle segment to create two tablettes comprising substantially different drugs (ignoring any inadvertent mixing between granulations). The current invention is most usefully employed after such optional tablet breaking through said middle segment, after which the first segment may then be itself subdivided if desired to create a plurality of accurately dosed tablettes.

The above example could as easily utilize a granulation compositionally substantially identical to said first granulation to enter (again) at the fourth filling station. Further segments could be added as a fifth segment and beyond, technical capacity for tablet production being the limiting factor. Furthermore, said second segment could comprise an active drug, or a mixture of the drug or drugs present in both the first and third segments in the example above, and the utility of the invention would persist, though relevance in medical or veterinary practice would relate to the nature of the drug or drugs in said middle segment.

A less preferred embodiment is as follows. A first granulation comprising a drug enters into a tablet die. An embossing that is 0.3 mm high bisects the lower punch. A second, inactive granulation enters said die above said first granulation. The tablet is compressed. The first segment is one (1.0) mm high after final compression. Thus the score, is 30% of the way through said first segment. The tablet has immediate release characteristics. The tablet is novel but lacks substantial advantages over tablets known in the art that lack a substantially inactive segment, but the second segment, does provide structural support for the tablet, so there may be some advantage.

The invention thus teaches novel methods of manufacture of deep scores within pharmacologically active parts of the tablet. Preferred methods of manufacture of the tablets of the invention that utilize an embossed bottom punch to produce the scored segment that is the subject of the invention utilize an upper punch that does not have any embossing, or else has an embossing of a small vertical dimension, above the embossing present on and extending upwards from the base of said lower punch.

A different mode of manufacture may be employed, using an embossed upper punch and a preferably flat-faced lower punch. In this technique, a most preferred tablet of the invention may be produced as follows. A first, inactive granulation enters the die and is optionally tamped. A second granulation comprising drug then enters the die, is optionally tamped, and final, compression occurs. Some amount of drug lies under the lower part of said embossing but the bulk of second granulation is apart from the breaking area, and thus when and if force is applied in a conventional, vertical fashion to the lowest aspect of the score, highly accurate tablet breaking will take place with respect to the active drug.

Tablets of the above design are not limited to two segments. A segment represents a contiguous part of a tablet of the invention that is formed from one granulation entering the tablet die at a time, with exceptions such as the following: If two successive granulations comprised the same active drug and similar excipients, then when compressed, they would comprise one segment. If, however, two different active drugs, such as different active drugs or different salts of the same active drug, were compressed onto each other, they would comprise two segments. Granulations comprising the same active drug but with dissimilar excipients would comprise two segments if one granulation were compressed onto another.

Benefits of the invention are not limited to tablets of any specific number of active ingredients. All segments containing an active ingredient may contain the same drug, or segments may contain different drugs.

In order to fully realize the benefits of the invention, a score may be placed into a segment (or interface between segments) of the tablet. This score may be formed in an inner segment with a file in a substantially horizontal manner, so that breaking the tablet through said score could lead to breaking through the inner segment while leaving the outer segments intact.

A further embodiment includes a unitary segment configuration wherein the embossed or post-production score is configured completely through an outer, e.g., bottom segment.

In addition, similar means of marking tablets may be followed such as by causing an edible ink to be placed on the tablets, thus delineating a desired region of the tablet, such as its middle segment. Such application is well known in the art. Other means of applying indicia are contemplated as within the scope of the invention.

Preferred tablets of the invention often use a height and an effective height H that are both over 4 mm, and may exceed 6 mm. Lesser heights and effective heights are utilized when needed due to size constraints on the tablet.

DESCRIPTION OF MANUFACTURE OF PREFERRED EMBODIMENTS

Example 1

Combination Metoprolol Succinate and Hydrochlorothiazide (HCTZ) Tablet

A combination metoprolol succinate and hydrochlorothiazide (HCTZ) tablet can be made which has three segments: (1) an active top or upper segment and (2) an active lower or bottom segment separated by (3) a substantially inactive middle segment. A Stokes 27-station tri-layer rotary tablet press can be used for layering the segments of the tablet.

All formulations comprise directly compressible compositions, and are manufactured using conventional techniques and processes, as are well known in the pharmaceutical manufacturing art. For example, powder blend formulations can be performed in a Patterson-Kelly "V" blender. Coatings can be applied by any means commonly known in the industry, however, if the anti-sticking agent is to be dusted onto the cores during the coating process, it is preferred to use a rotary granulator or pan coater for the coating process. If the anti-sticking agent is applied by suspending it in the coating solution, it is preferred to use a fluidized bed coater or rotary granulator for the coating process.

The middle, inactive layer consists of 194 mg of Nu-Tab® and requires no blending.

The tablets are compressed using, for example, 0.131 inch by 0.3222 inch oval, concave tablet punches to a hardness of 35 kiloponds. The bottom segment is introduced first into the die. The tablet weight is 300 mg. Tablets so made are about 11 mm tall; the inactive middle segment varies from about 5-8 mm in height and a width of about 4-6 mm.

Formulations comprising each segment are as follows:

A. Bottom Segment

Start with metoprolol succinate 100% in the form of compact spherical granules having an average particle size of 0.42 mm. A polymeric mixture is dissolved in an organic solvent such as ethanol, isopropyl alcohol and/or methylene chloride. The granules are then coated using a spray process. The spraying can be carried out in a coating pan, but is preferably carried out in a fluidized bed.

400 g of the metoprolol succinate granules above with particles less than 0.63 mm were coated with

| Ethylcellulose 10 cps | 177.1 g |
| Hydroxypropylmethyl cellulose | 38.9 g |
| Acetyltributylcitrate | 24.0 g |
| Methylene chloride | 4094 g |
| Isopropylic alcohol | 1029 g |

An additional tablet mass is made by wet granulation of the dry mixture of microcrystalline cellulose and maize starch with the potato starch-water solution in a planetary mixer. The mass is dried and the particle size reduced. Equal amounts (150 g) of the active coated granules and additional granules are finally mixed with Mg-stearate 0.1% and compressed to form the bottom segment of the tablet.

B. Middle Segment

| Nu-Tab ® (Compressible sugar 30/35 N.F.) | 194.00 |

C. Top Segment

| Lactose 310 monohydrate | 42.03 mg |
| Hydrochlorothiazide | 50.00 mg |
| Crospovidone | 2.16 mg |
| Magnesium stearate | 0.54 mg |
| FD&C Red #40 Aluminum Lake | 0.27 mg |
| Total | .00 |

Manufacturing Instructions
1. Weigh each ingredient.
2. Screen each ingredient.
3. Triturate the color with the major diluent in geometric proportions using a suitable mixer.
4. Add the remaining ingredients, except the lubricant, to the color mixer from Step #3 and mix for desired time.
5. Add the lubricant to the blend from Step #4 and mix for desired time.
6. Add the blend to a suitable press fitted with the desired tooling and compress into tablets.

Tabletting Instructions
1. Place the powder for active layer in hopper #1.
2. Place the powder for placebo layer in hopper #2.
3. Place the powder for active layer in hopper #3.
4. Compress layer #1 tablets to desired weight (tablets for layer #1 should form a soft compact).
5. Compress layer #1 & layer #2 tablets to desired combined weight of layer #1 and layer #2 weight (tablets should form a soft compact).
6. Compress the tri-layer tablet to the desired total tablet weight (layer #1 weight+layer #2 weight+layer #3 weight) Tablet should be at desired hardness.

A similar tablet of the invention is separately produced using the same top and bottom segments as the above, but using the following ingredients instead of Nu-Tab® for the middle segment. The following are blended using a Patterson-Kelly "V" blender.

| Ingredients for middle segment: | Mg. |
|---|---|
| Dibasic calcium phosphate anhydrous | 158.59 |
| Magnesium stearate | 2.79 |
| PVP K-30 | 2.62 |
| Total | 164.00 |

Manufacturing Instructions
1. Weigh each ingredient.
2. Screen each ingredient.
3. Place all of the ingredients, except the lubricant, into a suitable mixer and mix for desired time.
4. Add the lubricant to the blend from Step #3 and mix for desired time.
5. Add the blend to a suitable press fitted with the desired tooling and compress into tablets.

The tablets are compressed using oval 0.131 inch by 0.3222 inch, concave tablet punches to a hardness of 35 kiloponds. The bottom segment is introduced first, into the die. The tablet weight was 280 mg. Tablets with said middle segment are 6 mm high, and the inactive middle segment is 3.5-4 mm high.

Tabletting Instructions
1. Place the powder for active layer in hopper #1.
2. Place the powder for placebo layer in hopper #2.
3. Place the powder for active layer; in hopper #3.
4. Compress layer #1 tablets to desired weight (tablets for layer #1 should form a soft compact).
5. Compress layer #1 & layer #2 tablets to desired combined weight of layer #1 and layer #2 weight (tablets should form a soft compact).
6. Compress the tri-layer tablet to the desired total tablet weight (layer if 1 weight+layer #2 weight+layer #3 weight) Tablet should be at desired hardness.

In a similar way, other "taller-than-wide tablets may be made on a tablet press, such as the Korsch TRP900, which can produce taller tablets due to its design for deep filling cams which allow for deeper fills and greater distances between the upper and lower compression tools.

To make an oval 0.131 inch by 0.3222 inch, concave tablet that is 12 mm tall on the Korsch TRP900 the formulator would have to increase the weight of the inactive Nu-Tab® middle segment to about 323 mg. Similarly, to have a finished tablet height of 14 mm the tablet would be formulated with a middle segment weighing about 388 mg. If preferred, the formulator could, use the second example for a middle layer, i.e., the dibasic calcium phosphate (DCP) formulation. In such a case making an oval 0.131 inch by 0.3222 inch, concave tablet that is 12 mm tall on the Korsch TRP900 the formulator would have to increase the weight of the inactive DCP middle segment to about 410 mg. Similarly to have a finished tablet height of 14 mm the tablet would be formulated with a middle segment weighing about 492 mg.

The invention also includes the method of administering one or more drugs via the dosage forms such as tablets and tablettes of the invention to a patient, mammal, or other animal in need of pharmaceuticals for the prevention or treatment, of an illness, maintenance of good health, retarding of aging, or other purpose. Included are methods of treating a patient with only one drug from a combination product, such as with a novel tablette of the invention, enabling downward dose adjustment for a variety of reasons; or, in a similar vein, a patient may be treated with one whole tablet containing a plurality of active drugs and in addition receive only one drug from a similar tablet, thus enabling upward dose adjustment. Combination products that can benefit from the invention, in which one drug is in an outer active segment, and a second and different drug is in the other outer active segment, and a pharmacologically ineffective inner segment as in embodiments such as was described above, include those containing the following pairs of drugs: amlodipine and either benazepril, chlorthalidone, or atorvastatin; benazepril and hydrochlorothiazide; olmesartan and hydrochlorothiazide; and many others, including the majority of the currently-produced combination products. Also included is the method of treating a patient with a precise partial dose of medication from a whole tablet, which may be a half or quarter of the whole dose, but may usefully be a different fraction.

The following list, of possible combinations of a plurality of drugs is exemplary and not limiting. The combinations referred to may include two or more members of the classes listed. Drugs listed below, and herein, may for convenience exclude mention of any salt of a drug; e.g., "atorvastatin" is listed even though its marketed form is atorvastatin calcium.

Without limitation, useful combinations may include a plurality of drugs from within the following six drug classes. In addition, tablets of the invention may be created containing only one drug from the following list. With regards to combination use, two methods of use may apply to the invention. One of these methods is to place an individual drug in a granulation and a different individual drug (or combination of drugs) in a different granulation, potentially with an inactive granulation interposed between them; another method is to place a plurality of drugs in one or more segments.

No representation exists of any of the specific drug examples listed below are able to be created in an intrinsically altered release composition that is pharmaceutically acceptable.

1. Anti-anginal agents, for example:
   A. Calcium antagonists (see list below);
   B. Beta-blocker (see list below);
   C. Organic nitrate preparation (e.g., isosorbide mononitrate or dinitrate).

2. Anti-anginal agent plus an anti-platelet agent, such as aspirin, clopidogrel, or ticlopidine.
3. Two hypoglycemic agents (see list below),
4. Potassium chloride and any thiazide-type or loop diuretic (see lists below).
5. Lipid-lowering agent plus: hypoglycemic agent, anti-platelet agent, anti-anginal agent, and/or antihypertensive agent (see lists above and below)

Hypoglycemic: agents include: thiazolidinediones: pioglitazone, rosiglitazone; sulfonylureas: glyburide, glipizide, glimepiride, chlorpropamide;
Biguanides: metformin;
Meglitinides: nateglinide, repaglinide;
Glucosidase inhibitors; acarbose, miglitol.
6. Antihypertensive agents:
Beta-blockers: acebutolol, atenolol, bisoprolol, celiprolol, metoprolol, mebivolol, carvedilol (a mixed alpha-beta blocker), nadolol, oxprenolol, penbutolol, pindolol, propranolol, timolol, betaxolol, cartcolol;
Calcium antagonists (calcium-channel blockers): nifedipine, amlodipine, verapamil, diltiazem, nisoldipine, felodipine, isradipine, lacidipine, lercanidipine, nicardipine, manidipine;
Thiazide-type diuretics (with or without potassium-retaining diuretics such as triamterene, amiloride, or spironolactone): hydrochlorothiazide, chlorothiazide, cyclopenthiazide, polythiazide, bendrofluazide, hydroflumethiazide, chlorthalidone, indapamide, methylclothiazide, metolazone;
Angiotensin converting enzyme inhibitors: captopril, enalapril, lisinopril, ramipril, trandolapril, quinapril, perindopril, moexipril, benazepril, fosinopril;
Angiotensin receptor blockers: losartan, valsartan, candesartan, telmisartan, eprosartan, irbesartan;
High-ceiling (loop) diuretics (with or without potassium-retaining diuretics such as triamterene, amiloride, or spironolactone): furosemide, torsemide, ethacrynic acid, bumetamide;
Aldosterone antagonist diuretics: spironolactone, eplerenone;
Alpha-blockers: doxazosin, terazosin, prazosin, indoramin, labetolol (a mixed alpha-beta blocker);
Central alpha-agonists: clonidine, methyldopa;
Imidazoline: moxonidine;
Direct vasodilators: hydralazine, minoxidil;
Adrenergic neuronal blocker: guanethidine.
Lipid-lowering agents include:
Statins: lovastatin, simvastatin, pravastatin, rosuvastatin, atorvastatin, fluvastatin;
Fibrates: clofibrate, bezafibrate, fenofibrate, gemfibrozil, ciprofibrate;
Others: ezetimide, niacin, acipimox.

The combinations of drugs disclosed herein are for illustrative purposes and are not intended to limit the scope of the invention.

Regarding the important usage of the tablets and tablettes of the invention, that involving division of a tablet into tablettes containing similar active segments, most drugs that may undergo dosage adjustment will be preferred if they may be divided in an optimally precise manner. Examples of drugs that will especially benefit, from the advances of the invention in this manner include narrow therapeutic index drugs such as warfarin, digoxin, L-thyroxine; vasoactive drugs such as amlodipine; hypoglycemic agents such as rosiglitazone and glipizide; and anxiolytics drugs such as alprazolam. These are but a small fraction of the great number of drugs that will benefit from the various embodiments and procedures of the invention.

There are numerous methods of use of the dosage forms of the invention, including its tablets and tablettes. Persons skilled in the medical and pharmaceutical arts will recognize the many advantages that the various embodiments of the invention allow over current products. Some examples of benefits of the inventions involving tablets containing exactly one similar active segment are described immediately below.

A further benefit of the invention may relate to pediatric or geriatric doses, which may not be produced in appropriate dose strengths. In the case of amlodipine, a 1.25 mg daily dose may be useful in either small children with hypertension, or in frail elderly patients with angina or hypertension, who may have hepatic dysfunction. Even though the United. States Food and Drug Administration (FDA) has not approved a 1.25 mg dose, precise divisibility of the approved 2.5 mg dose would allow a 1.25 mg daily dose. In addition, precise divisibility of the approved 2.5 mg dose will allow accurate dosing of 3.75 mg daily.

Another use of the invention is to enable a method of cost savings to insurers and patients. The invention allows this because many drugs have pricing that differs little (if at all) between different doses. Because tablet splitting is imprecise for most scored tablets, the practice of mandatory splitting has been met with disapproval by most physician and pharmacist, organizations. The invention enables tablet splitting due to provide accurate dosing when a tablet (or some tablettes) of the invention are broken as described herein. Substantial benefits are foreseen from this innovation. In addition, the ability to separate one active drug from another. In a combination product has cost saving advantages, as well.

It is recognized that related inventions may be within the spirit of the disclosures herein. Also, no omission in the current application is intended to limit, the inventors to the current claims or disclosures. While certain preferred and alternative embodiments of the invention have been set forth for purposes of disclosing the invention, modifications to the disclosed embodiments may occur to those who are skilled in the art.

The invention claimed is:

1. A compressed, layered pharmaceutical dosage form comprising
    a first bottom segment comprising a composition containing an effective amount of one or more drugs, said segment comprising a score greater than 50% through the maximum height of said first segment and
    a second, unscored, top segment contacting said first segment, said second segment comprising a composition substantially free of drug, said second segment forming an outer segment of said dosage form and providing a breaking segment for breaking through said second segment without substantial consequent breakage of the first segment, wherein said tablet is compressed in a tablet compression die using an embossed bottom punch and an unembossed top punch to allow tamping of the first bottom segment by the unembossed top punch, and
    wherein the terms "upper," "lower," "top" and "bottom" refer to orientation of the segments or tablet in a tablet die during compression.

2. The dosage form of claim 1 wherein said composition containing a drug or drugs is a controlled release composition selected from the group consisting of delayed release, modified release, sustained-release, and quick dissolve oral or buccal release.

3. The pharmaceutical tablet of claim 1 comprising in at least one segment a colorant for visually distinguishing said segment from another segment.

4. The dosage form of claim 1 wherein said tablet is further covered with an inert or pharmaceutically inactive composition.

5. The dosage form of claim 4 wherein the inert or pharmaceutically inactive composition is a capsule.

* * * * *